United States Patent
Janna et al.

(10) Patent No.: US 8,570,187 B2
(45) Date of Patent: Oct. 29, 2013

(54) SYSTEM AND METHOD FOR COMMUNICATING WITH A TELEMETRIC IMPLANT

(75) Inventors: Sied W. Janna, Memphis, TN (US);
Darren James Wilson, York (GB);
Martin S. Goodchild, Reach (GB);
Peter A. Brady, Ely (GB)

(73) Assignee: Smith & Nephew, Inc., Memphis, TN (US)

( * ) Notice: Subject to any disclaimer, the term of this patent is extended or adjusted under 35 U.S.C. 154(b) by 418 days.

(21) Appl. No.: 12/675,826

(22) PCT Filed: Sep. 5, 2008

(86) PCT No.: PCT/US2008/075316
§ 371 (c)(1),
(2), (4) Date: May 13, 2011

(87) PCT Pub. No.: WO2009/032969
PCT Pub. Date: Mar. 12, 2009

(65) Prior Publication Data
US 2011/0205083 A1    Aug. 25, 2011

Related U.S. Application Data

(60) Provisional application No. 60/970,460, filed on Sep. 6, 2007.

(51) Int. Cl.
*G08C 19/00* (2006.01)

(52) U.S. Cl.
USPC ...... 340/870.31; 343/704; 343/713; 343/718; 343/788; 343/895; 375/150; 600/302; 600/407; 600/511; 600/595; 455/98; 367/76; 367/79; 336/192; 336/197; 336/198; 340/669; 340/318; 340/870.16; 340/870.13; 340/870.26

(58) Field of Classification Search
USPC .............. 340/669, 318, 319, 870.16, 870.13, 340/870.18, 870.26, 870.07, 870.23, 340/870.04; 343/704, 713, 718, 788, 895; 607/61, 115; 375/150; 600/302, 407, 600/511, 595; 455/41.1, 98; 367/76, 79; 336/192, 197, 198
See application file for complete search history.

(56) References Cited

U.S. PATENT DOCUMENTS

| | | |
|---|---|---|
| 3,713,148 A | 1/1973 | Cardullo et al. |
| 3,727,209 A | 4/1973 | White et al. |

(Continued)

FOREIGN PATENT DOCUMENTS

| | | |
|---|---|---|
| CN | 1127446 A | 7/1996 |
| CN | 101022760 A | 8/2007 |

(Continued)

OTHER PUBLICATIONS

Fruin, et al, "Validity of a Multi-Sensor Armband in Estimating Rest and Exercise Energy Expenditure", Am Coll Sports Med, vol. 36, 6, pp. 1063-1069, 2004.

(Continued)

*Primary Examiner* — Lam T Mai
(74) *Attorney, Agent, or Firm* — Fish & Richardson P.C.

(57) ABSTRACT

A telemetric system includes a telemetric implant, a reader unit adapted to read signals from the telemetric implant, and an antenna adapted for connection to the reader unit and to receive signals from the telemetric implant. The antenna has a first coil, a second coil, and a connector. The first coil is electrically connected to the second coil, and the connector allows for movement of the first and second coils relative to each other. The antenna may be used to send radio-frequency power to the telemetric implant and receives data from the telemetric implant.

17 Claims, 21 Drawing Sheets

(56) References Cited

U.S. PATENT DOCUMENTS

| | | | |
|---|---|---|---|
| 3,976,060 A | 8/1976 | Hildebrandt et al. |
| 4,096,477 A | 6/1978 | Epstein et al. |
| 4,242,663 A | 12/1980 | Slobodin |
| 4,281,664 A | 8/1981 | Duggan |
| 4,361,153 A | 11/1982 | Slocum et al. |
| 4,441,498 A | 4/1984 | Nordling |
| 4,473,825 A | 9/1984 | Walton |
| 4,481,428 A | 11/1984 | Charlot |
| 4,494,545 A | 1/1985 | Slocum et al. |
| 4,510,495 A | 4/1985 | Sigrimis et al. |
| 4,513,743 A | 4/1985 | van Arragon et al. |
| 4,525,713 A | 6/1985 | Barletta et al. |
| 4,546,241 A | 10/1985 | Walton |
| 4,571,589 A | 2/1986 | Slocum et al. |
| 4,576,158 A | 3/1986 | Boland |
| 4,944,299 A | 7/1990 | Silvian |
| 4,952,928 A | 8/1990 | Carroll et al. |
| 4,991,682 A | 2/1991 | Kuntz et al. |
| 5,024,239 A | 6/1991 | Rosenstein |
| 5,030,236 A | 7/1991 | Dean |
| 5,042,504 A | 8/1991 | Huberti |
| 5,117,825 A | 6/1992 | Grevious |
| 5,197,488 A | 3/1993 | Kovacevic |
| 5,252,962 A | 10/1993 | Urbas et al. |
| 5,309,919 A | 5/1994 | Snell et al. |
| 5,326,363 A | 7/1994 | Aikins |
| 5,330,477 A | 7/1994 | Crook |
| 5,334,202 A | 8/1994 | Carter |
| 5,337,747 A | 8/1994 | Neftel |
| 5,360,016 A | 11/1994 | Kovacevic |
| 5,383,935 A | 1/1995 | Shirkhanzadeh |
| 5,416,695 A | 5/1995 | Stutman et al. |
| 5,423,334 A | 6/1995 | Jordan |
| 5,425,775 A | 6/1995 | Kovacevic |
| 5,456,724 A | 10/1995 | Yen et al. |
| 5,470,354 A | 11/1995 | Hershberger et al. |
| 5,481,262 A | 1/1996 | Urbas et al. |
| 5,533,519 A | 7/1996 | Radke et al. |
| 5,626,630 A | 5/1997 | Markowitz et al. |
| 5,630,835 A | 5/1997 | Brownlee |
| 5,681,313 A | 10/1997 | Diez |
| 5,695,496 A | 12/1997 | Orsak et al. |
| 5,720,746 A | 2/1998 | Soubeiran |
| 5,733,292 A | 3/1998 | Gustilo |
| 5,735,887 A | 4/1998 | Barreras et al. |
| 5,741,315 A | 4/1998 | Lee et al. |
| 5,792,076 A | 8/1998 | Orsak et al. |
| 5,807,701 A | 9/1998 | Payne et al. |
| 5,833,603 A | 11/1998 | Kovacs et al. |
| 5,836,989 A | 11/1998 | Shelton |
| 5,873,843 A | 2/1999 | Draper |
| 5,904,708 A | 5/1999 | Goedeke |
| 5,935,171 A | 8/1999 | Schneider et al. |
| 5,944,745 A | 8/1999 | Rueter |
| 6,009,878 A | 1/2000 | Weijand et al. |
| 6,025,725 A | 2/2000 | Gershenfeld et al. |
| 6,034,295 A | 3/2000 | Rehberg et al. |
| 6,034,296 A | 3/2000 | Elvin et al. |
| 6,059,576 A | 5/2000 | Brann |
| 6,061,597 A | 5/2000 | Riemann et al. |
| 6,102,874 A | 8/2000 | Stone et al. |
| 6,111,520 A | 8/2000 | Allen et al. |
| 6,120,502 A | 9/2000 | Michelson |
| 6,135,951 A | 10/2000 | Richardson et al. |
| 6,143,035 A | 11/2000 | McDowell |
| 6,168,569 B1 | 1/2001 | McEwen et al. |
| 6,200,265 B1 | 3/2001 | Walsh et al. |
| 6,201,980 B1 | 3/2001 | Darrow et al. |
| 6,206,837 B1 * | 3/2001 | Brugnoli ............ 600/529 |
| 6,210,301 B1 | 4/2001 | Abraham-Fuchs et al. |
| 6,245,109 B1 | 6/2001 | Mendes et al. |
| 6,312,612 B1 | 11/2001 | Sherman et al. |
| 6,325,756 B1 | 12/2001 | Webb et al. |
| 6,327,501 B1 | 12/2001 | Levine et al. |
| 6,334,072 B1 * | 12/2001 | Leysieffer ............ 607/57 |
| 6,356,789 B1 | 3/2002 | Hinssen et al. |
| 6,369,694 B1 | 4/2002 | Mejia |
| 6,385,593 B2 | 5/2002 | Linberg |
| 6,402,689 B1 | 6/2002 | Scarantino et al. |
| 6,405,088 B1 | 6/2002 | Merlin et al. |
| 6,433,629 B2 | 8/2002 | Hamel et al. |
| 6,434,429 B1 | 8/2002 | Kraus et al. |
| 6,442,432 B2 | 8/2002 | Lee |
| 6,447,448 B1 | 9/2002 | Ishikawa et al. |
| 6,447,449 B1 | 9/2002 | Fleischman et al. |
| 6,449,508 B1 | 9/2002 | Sheldon et al. |
| 6,466,810 B1 | 10/2002 | Ward et al. |
| 6,477,424 B1 | 11/2002 | Thompson et al. |
| 6,482,154 B1 | 11/2002 | Haubrich et al. |
| 6,497,655 B1 | 12/2002 | Linberg et al. |
| 6,499,488 B1 | 12/2002 | Hunter et al. |
| 6,522,916 B1 * | 2/2003 | Kwon ............ 600/511 |
| 6,527,711 B1 | 3/2003 | Stivoric et al. |
| 6,529,127 B2 | 3/2003 | Townsend et al. |
| 6,535,766 B1 | 3/2003 | Thompson et al. |
| 6,539,253 B2 | 3/2003 | Thompson et al. |
| 6,553,262 B1 | 4/2003 | Lang et al. |
| 6,567,703 B1 | 5/2003 | Thompson et al. |
| 6,573,706 B2 | 6/2003 | Mendes et al. |
| 6,583,630 B2 | 6/2003 | Mendes et al. |
| 6,602,191 B2 | 8/2003 | Quy |
| 6,610,096 B2 | 8/2003 | MacDonald |
| 6,636,769 B2 | 10/2003 | Govari et al. |
| 6,638,231 B2 | 10/2003 | Govari et al. |
| 6,641,540 B2 | 11/2003 | Fleischman et al. |
| 6,652,464 B2 | 11/2003 | Schwartz et al. |
| 6,658,300 B2 | 12/2003 | Govari et al. |
| 6,667,725 B1 | 12/2003 | Simons et al. |
| 6,675,044 B2 | 1/2004 | Chen |
| 6,682,490 B2 | 1/2004 | Roy et al. |
| 6,694,180 B1 | 2/2004 | Boesen |
| 6,700,547 B2 * | 3/2004 | Mejia et al. ............ 343/743 |
| 6,706,005 B2 | 3/2004 | Roy et al. |
| 6,712,778 B1 | 3/2004 | Jeffcoat et al. |
| 6,734,831 B2 * | 5/2004 | Makino ............ 343/895 |
| 6,738,671 B2 | 5/2004 | Christophersom et al. |
| 6,749,568 B2 | 6/2004 | Fleischman et al. |
| 6,760,363 B1 * | 7/2004 | Bettaieb ............ 375/150 |
| 6,764,446 B2 | 7/2004 | Wolinsky et al. |
| 6,766,200 B2 | 7/2004 | Cox |
| 6,783,499 B2 | 8/2004 | Schwartz |
| 6,790,372 B2 | 9/2004 | Roy et al. |
| 6,793,659 B2 | 9/2004 | Putnam |
| 6,804,552 B2 | 10/2004 | Thompson et al. |
| 6,807,439 B2 | 10/2004 | Edwards et al. |
| 6,810,753 B2 | 11/2004 | Valdevit et al. |
| 6,819,247 B2 | 11/2004 | Bimbach et al. |
| 6,821,299 B2 | 11/2004 | Kirking et al. |
| 6,834,436 B2 | 12/2004 | Townsend et al. |
| 6,855,115 B2 | 2/2005 | Fonseca et al. |
| 6,864,802 B2 | 3/2005 | Smith et al. |
| 6,895,280 B2 | 5/2005 | Meadows |
| 6,895,281 B1 | 5/2005 | Amundson et al. |
| 6,926,670 B2 | 8/2005 | Rich et al. |
| 6,939,299 B1 | 9/2005 | Petersen et al. |
| 6,968,743 B2 | 11/2005 | Rich et al. |
| 6,994,672 B2 | 2/2006 | Fleischman et al. |
| 7,001,346 B2 | 2/2006 | White |
| 7,027,871 B2 | 4/2006 | Burnes et al. |
| 7,034,694 B2 | 4/2006 | Yamaguchi et al. |
| 7,061,400 B2 * | 6/2006 | Vet ............ 340/870.16 |
| 7,097,662 B2 | 8/2006 | Evans |
| 7,123,164 B2 * | 10/2006 | Zoladek et al. ............ 340/870.07 |
| 7,145,461 B2 | 12/2006 | Lehrman et al. |
| 7,147,604 B1 | 12/2006 | Allen et al. |
| 7,151,914 B2 | 12/2006 | Brewer |
| 7,182,736 B2 | 2/2007 | Roy |
| 7,190,273 B2 | 3/2007 | Liao et al. |
| 7,195,645 B2 | 3/2007 | DiSilvestro et al. |
| 7,209,790 B2 | 4/2007 | Thompson et al. |
| 7,212,133 B2 | 5/2007 | Goetz et al. |
| 7,218,232 B2 | 5/2007 | DiSilvestro |
| 7,229,415 B2 | 6/2007 | Schwartz |
| 7,256,695 B2 | 8/2007 | Hamel |

(56) References Cited

U.S. PATENT DOCUMENTS

| | | |
|---|---|---|
| 7,333,013 B2 | 2/2008 | Berger |
| 7,357,037 B2 | 4/2008 | Hnat et al. |
| 7,381,223 B2 | 6/2008 | Kovacevic |
| 7,474,223 B2 | 1/2009 | Nycz et al. |
| 7,559,951 B2 | 7/2009 | DiSilvestro et al. |
| 7,729,758 B2 | 6/2010 | Haller et al. |
| 7,756,579 B2 | 7/2010 | Nitzan et al. |
| 7,780,613 B2 | 8/2010 | Sherman |
| 7,786,895 B2 * | 8/2010 | Zoladek et al. .......... 340/870.07 |
| 8,007,450 B2 | 8/2011 | Williams |
| 2001/0047125 A1 | 11/2001 | Quy |
| 2002/0099359 A1 | 7/2002 | Santini, Jr. et al. |
| 2002/0116080 A1 | 8/2002 | Birnbach |
| 2002/0138153 A1 | 9/2002 | Koniuk |
| 2002/0151978 A1 | 10/2002 | Zacouto et al. |
| 2002/0170193 A1 | 11/2002 | Townsend et al. |
| 2003/0040806 A1 | 2/2003 | MacDonald |
| 2003/0069644 A1 | 4/2003 | Kovacevic et al. |
| 2003/0105470 A1 | 6/2003 | White |
| 2003/0120150 A1 | 6/2003 | Govari |
| 2003/0136417 A1 | 7/2003 | Fonseca |
| 2003/0143775 A1 | 7/2003 | Brady |
| 2003/0178488 A1 | 9/2003 | Southard |
| 2003/0229381 A1 | 12/2003 | Hochmair et al. |
| 2004/0008123 A1 | 1/2004 | Carrender et al. |
| 2004/0011137 A1 | 1/2004 | Hnat et al. |
| 2004/0014456 A1 | 1/2004 | Vaananen |
| 2004/0019382 A1 | 1/2004 | Amirouche |
| 2004/0073137 A1 | 4/2004 | Lloyd et al. |
| 2004/0073221 A1 | 4/2004 | Biscup |
| 2004/0094613 A1 | 5/2004 | Shiratori et al. |
| 2004/0113790 A1 | 6/2004 | Hamel et al. |
| 2004/0116837 A1 | 6/2004 | Yamaguchi et al. |
| 2004/0152972 A1 | 8/2004 | Hunter |
| 2004/0176815 A1 | 9/2004 | Janzig et al. |
| 2004/0186396 A1 | 9/2004 | Roy et al. |
| 2004/0204647 A1 | 10/2004 | Grupp et al. |
| 2004/0231420 A1 | 11/2004 | Xie et al. |
| 2004/0243148 A1 | 12/2004 | Wasielewski |
| 2004/0249315 A1 | 12/2004 | Damen |
| 2005/0010139 A1 | 1/2005 | Aminian et al. |
| 2005/0010299 A1 | 1/2005 | Disilvestro et al. |
| 2005/0010300 A1 | 1/2005 | Disilvestro et al. |
| 2005/0010301 A1 | 1/2005 | Disilvestro et al. |
| 2005/0010302 A1 | 1/2005 | Dietz et al. |
| 2005/0012610 A1 | 1/2005 | Liao et al. |
| 2005/0012617 A1 | 1/2005 | DiSilvestro et al. |
| 2005/0015014 A1 | 1/2005 | Fonseca et al. |
| 2005/0061079 A1 | 3/2005 | Schulman |
| 2005/0080335 A1 | 4/2005 | Simon et al. |
| 2005/0099290 A1 | 5/2005 | Govari |
| 2005/0101833 A1 | 5/2005 | Hsu et al. |
| 2005/0113932 A1 | 5/2005 | Kovacevic |
| 2005/0131397 A1 | 6/2005 | Levin |
| 2005/0187482 A1 | 8/2005 | O'Brien et al. |
| 2005/0194174 A1 | 9/2005 | Hipwell, Jr. et al. |
| 2005/0234555 A1 | 10/2005 | Sutton et al. |
| 2005/0247319 A1 | 11/2005 | Berger |
| 2005/0273170 A1 | 12/2005 | Navarro et al. |
| 2005/0288727 A1 | 12/2005 | Penner |
| 2006/0009656 A1 | 1/2006 | Zhang |
| 2006/0009856 A1 | 1/2006 | Sherman et al. |
| 2006/0030771 A1 | 2/2006 | Levine |
| 2006/0032314 A1 | 2/2006 | Hnat et al. |
| 2006/0043178 A1 | 3/2006 | Tethrake et al. |
| 2006/0043179 A1 | 3/2006 | Nycz et al. |
| 2006/0047283 A1 | 3/2006 | Evans, III et al. |
| 2006/0052782 A1 | 3/2006 | Morgan et al. |
| 2006/0058627 A1 | 3/2006 | Flaherty |
| 2006/0065739 A1 | 3/2006 | Falls et al. |
| 2006/0069436 A1 | 3/2006 | Sutton et al. |
| 2006/0069447 A1 | 3/2006 | Disilvestro et al. |
| 2006/0095135 A1 | 5/2006 | Kovacevic |
| 2006/0109105 A1 | 5/2006 | Varner et al. |
| 2006/0111291 A1 | 5/2006 | DiMauro et al. |
| 2006/0119481 A1 | 6/2006 | Tethrake et al. |
| 2006/0129050 A1 | 6/2006 | Martinson et al. |
| 2006/0142656 A1 | 6/2006 | Malackowski et al. |
| 2006/0145871 A1 | 7/2006 | Donati et al. |
| 2006/0174712 A1 | 8/2006 | O'Brien et al. |
| 2006/0177956 A1 | 8/2006 | O'Brien et al. |
| 2006/0190080 A1 | 8/2006 | Danoff et al. |
| 2006/0196277 A1 | 9/2006 | Allen et al. |
| 2006/0200030 A1 | 9/2006 | White et al. |
| 2006/0200031 A1 | 9/2006 | White et al. |
| 2006/0232408 A1 | 10/2006 | Nycz et al. |
| 2006/0235310 A1 | 10/2006 | O'Brien et al. |
| 2006/0241354 A1 | 10/2006 | Allen |
| 2006/0244465 A1 | 11/2006 | Kroh et al. |
| 2006/0260401 A1 | 11/2006 | Xie |
| 2006/0271199 A1 | 11/2006 | Johnson |
| 2006/0283007 A1 | 12/2006 | Cros et al. |
| 2006/0287602 A1 | 12/2006 | O'Brien et al. |
| 2006/0287700 A1 | 12/2006 | White et al. |
| 2007/0038051 A1 | 2/2007 | Talman et al. |
| 2007/0078497 A1 | 4/2007 | Vandanacker |
| 2007/0089518 A1 | 4/2007 | Ericson et al. |
| 2007/0090543 A1 | 4/2007 | Condie et al. |
| 2007/0100215 A1 | 5/2007 | Powers et al. |
| 2007/0123938 A1 | 5/2007 | Haller et al. |
| 2007/0129769 A1 | 6/2007 | Bourget et al. |
| 2007/0180922 A1 | 8/2007 | Crottet et al. |
| 2007/0208544 A1 | 9/2007 | Kulach et al. |
| 2007/0219639 A1 | 9/2007 | Otto et al. |
| 2008/0080335 A1 | 4/2008 | Matsumoto et al. |
| 2008/0086145 A1 | 4/2008 | Sherman et al. |
| 2008/0105874 A1 | 5/2008 | Wang et al. |
| 2008/0161729 A1 | 7/2008 | Bush |
| 2008/0208516 A1 | 8/2008 | James |
| 2008/0300597 A1 | 12/2008 | Morgan et al. |
| 2009/0222050 A1 | 9/2009 | Wolter et al. |

FOREIGN PATENT DOCUMENTS

| | | |
|---|---|---|
| DE | 19855254 | 6/2000 |
| EP | 0062459 | 12/1986 |
| EP | 1023872 | 8/2000 |
| EP | 1099415 | 5/2001 |
| EP | 0959956 | 12/2001 |
| EP | 1256316 | 11/2002 |
| EP | 1309960 | 5/2003 |
| EP | 1331903 | 8/2003 |
| EP | 1366712 | 12/2003 |
| EP | 1495456 | 1/2005 |
| EP | 1502540 | 2/2005 |
| EP | 0987047 | 4/2005 |
| EP | 1535039 | 6/2005 |
| EP | 1541095 | 6/2005 |
| EP | 1570781 | 9/2005 |
| EP | 1570782 | 9/2005 |
| EP | 1582183 | 10/2005 |
| EP | 1586287 | 10/2005 |
| EP | 1611835 | 1/2006 |
| EP | 1642550 | 4/2006 |
| EP | 1704893 A1 | 9/2006 |
| EP | 1738716 A2 | 1/2007 |
| EP | 1765204 | 3/2007 |
| EP | 1377340 | 5/2007 |
| EP | 1803394 | 7/2007 |
| EP | 1830303 | 9/2007 |
| JP | 03-231628 | 10/1991 |
| JP | 07-255683 | 10/1995 |
| JP | 11-216154 | 8/1999 |
| JP | 2001-309892 | 11/2001 |
| JP | 2002-095638 | 4/2002 |
| JP | 2003-102692 | 4/2003 |
| JP | 2007-124307 | 5/2007 |
| WO | 82/00378 | 2/1982 |
| WO | 90/06720 | 6/1990 |
| WO | WO9621397 A1 | 7/1996 |
| WO | 96/26678 | 9/1996 |
| WO | 96/29007 | 9/1996 |
| WO | 97/14367 | 4/1997 |
| WO | 97/20512 | 6/1997 |

(56) References Cited

FOREIGN PATENT DOCUMENTS

| | | |
|---|---|---|
| WO | WO9843701 A1 | 10/1998 |
| WO | 00/18317 | 4/2000 |
| WO | 00/19888 | 4/2000 |
| WO | 00/30534 | 6/2000 |
| WO | 00/32124 | 6/2000 |
| WO | 01/19248 | 3/2001 |
| WO | 01/37733 | 5/2001 |
| WO | 02/03347 | 1/2002 |
| WO | 02/38082 | 5/2002 |
| WO | 02/056763 | 7/2002 |
| WO | 02/058551 | 8/2002 |
| WO | 02/061705 | 8/2002 |
| WO | 03/003145 | 1/2003 |
| WO | 03/008570 | 1/2003 |
| WO | 03/044556 | 5/2003 |
| WO | 03/085617 | 10/2003 |
| WO | 2004/005872 | 1/2004 |
| WO | 2004/014456 | 2/2004 |
| WO | 2004/052453 | 6/2004 |
| WO | 2004/052456 | 6/2004 |
| WO | 2004/077073 | 9/2004 |
| WO | 2005/007025 | 1/2005 |
| WO | 2005/013851 | 2/2005 |
| WO | 2005/039440 | 5/2005 |
| WO | 2005/074821 | 8/2005 |
| WO | 2005/084544 | 9/2005 |
| WO | 2005/104997 | 11/2005 |
| WO | 2005/120203 | 12/2005 |
| WO | 2006/010037 | 1/2006 |
| WO | 2006/045080 | 4/2006 |
| WO | 2006/045607 | 5/2006 |
| WO | 2006/049796 | 5/2006 |
| WO | 2006/052765 | 5/2006 |
| WO | 2006/055547 | 5/2006 |
| WO | 2006/063156 | 6/2006 |
| WO | 2006/086113 | 8/2006 |
| WO | 2006/086114 | 8/2006 |
| WO | 2006/089069 | 8/2006 |
| WO | 2006/094273 | 9/2006 |
| WO | 2006/096582 | 9/2006 |
| WO | 2006/110798 | 10/2006 |
| WO | 2006/113660 | 10/2006 |
| WO | WO2006131302 A1 | 12/2006 |
| WO | 2007/002185 | 1/2007 |
| WO | 2007/002224 | 1/2007 |
| WO | 2007/002225 | 1/2007 |
| WO | 2007/008493 | 1/2007 |
| WO | 2007/009088 | 1/2007 |
| WO | 2007/025191 | 3/2007 |
| WO | 2007/030489 | 3/2007 |
| WO | 2007/036318 | 4/2007 |
| WO | WO2007041124 A1 | 4/2007 |
| WO | 2007/061890 | 5/2007 |
| WO | 2007/090543 | 8/2007 |
| WO | 2008/105874 | 9/2008 |
| WO | 2009/098768 | 8/2009 |

OTHER PUBLICATIONS

Jakicic, et al, "Evaluation of the SenseWear Pro Armband™ to Assess Energy Expenditure during Exercise", Med. Sci. Sports Exerc.; vol. 36,5, pp. 897-904, 2004.

Nachemson et al., "Intravital wireless telemetry of axial forces in Harrington distraction rods in patients with idiopathic scoliosis", J.Bone Jt Surg. 53A, 445-464 (Apr. 1971).

Burny, et al., "Smart orthopedic implants", Orthopedics, Dec. 2005; 28 (12):1401.

Rydell, "Forces Acting on the Femoral Head Prosthesis", Acta Orthop Scand, Suppl. 88, 1966.

Lanyon, et al., "In Vivo Strain Measurements from Bone and Prosthesis following Total Hip Replacement", The Journal of Bone and Joint Surgery, vol. 63-A, No. 6, pp. 989-1000, 1981.

Carlson, et al., "A Radio Telemetry Device for Monitoring Cartilage Surface Pressures in the Human Hip", IEEE Trans. on Biomed. Engrg., vol. BME-21, No. 4, pp. 257-264, Jul. 1974.

Carlson, et al, "A look at the prosthesis-cartilage interface: design of a hip prosthesis containing pressure transducers", J Biomed Mater Res. 1974; 8(4 pt 2): 261-269.

English, et al., "In vivo records of hip loads using a femoral implant with telemetric output (a preliminary report)," J Biomed Eng. 1979; 1(2):111-115.

Rushfeldt, et al., Improvd Techniques for Measuring in Vitro Geometry and Pressure Distribution in Human Acetabulum-II. Instrumented . . . J Biomechanics No. 14, pp. 315-323, 1981.

Hodge, et al., "Preliminary in Vivo Pressure Measurements in a Human Acetabulum", Proceedings of 31 st Annual Meeting, Orthopaedic Research Society, 1985.

Hodge, et al., "Contact Pressures in the Human Hip Joint Measured in Vivo", Proc. of National Academy of Science, U.S.A., No. 83, pp. 2879-2883, 1986.

Brown, et al., "In Vivo Load Measurements on a Total Hip Prosthesis", Proceedings of the 31 st Meeting, Orthopaedic Research Society, 1985.

Davy, et al., "Telemetric Force Measurements across the Hip after Total Arthroplasty", Journal of Bone and Joint Surgery, vol. 70-A, No. 1, Jan. 1988: 45-50.

Taylor, et al., "Telemetry of forces from proximal femoral replacements and relevance to fixation", J Biomech. 1997; 30:225-234.

Bergmann, et al., "Multichannel Strain Gauge Telemetry for Orthopaedic Implants", Technical Note, J. Biomechanics, vol. 21, No. 2, pp. 169-176, 1988.

Rohlmann, et al., "Telemeterized Load Measurement Using Instrumented Spinal Internal Fixators in a Patient with Degenerative Instability", Spine, vol. 20, No. 24, 1995.

Berkman, et al., "Biomedical Micropressor with Analog I/0", Inter. Solid-State Circuits Conf. Digest of Technical Papers, pp. 168-169, 1981.

Dorman, et al., "A Monolithic Signal Processor for a Neurophysiological Telemetry System", IEEE Journal of Solid-State Circuits, vol. 20, pp. 1185-1193, 1985.

Gschwend, et al., "A General Purpose Implantable Multichannel Telemetry System for Physiological Research", Biotelemetry Patient Monitoring, vol. 6, pp. 107-117, 1979.

Cook, et al., "A Custom Microprocessor for Implantable Telemetry Systems", Proc of the IEEE Symp. on Computer-Based Medical Systems, pp. 412-417, Jun. 1990.

Brown, et al., "Telemetering *In Vivo* Loads from Nail Plate Implants", J. Biomechanics, vol. 15, No. 11, pp. 815-823, 1982.

Fernald, et al., "A System Architecture for Intelligent Implantable Biotelemetry Instruments", Proc. IEEE Eng in Medicine and Biology Soc. Annual Conf., pp. 1411-1412, 1989.

Rohlmann, et al., "Influence of load carrying on loads in internal spinal fixators", J Biomech. 2000; 33:1099-1104.

Rohlmann, et al., "Loads on an internal spinal fixation device during walking", J Biomech, 1997; 30:41-47.

Schneider, et al, "Loads acting in an intramedullary nail during fracture healing in the human femur", Journal of Biomechanics 34, 2001, pp. 849-857.

Heinlein, et al., "An instrumented knee endoprosthesis for measuring loads in vivo", EORS 2004, 51st Annual Meeting of the Orthopaedic research Society, Aug. 2007, 1 page.

Townsend, et al., Multichannel, Programmable, Microprocessor Based Strain Gauge . . . , 18th Ann. Int Conf. IEEE Eng. in Med & Biology Soc. Oct. 31-Nov. 3, 1996, Amsterdam.

Mendes, et al., "IntelliJoint System for monitoring displacement in biologic system", Biomed Bytes 2002 (4), pp. 69-70.

Cristofolini, et al., "A novel transducer for the measurement of cement-prosthesis interface forces in cemented . . . ", Medicial Eng & Physics vol. 22, Sep. 7, 2000, pp. 493-501.

Müller, Otto, et al., "Three-dimensional measurements of the pressure distribution in artificial joints with a capacitive sensor array", J Biomech, vol. 37, Oct. 2004, pp. 1623-1625.

Bergmann, et al., "Frictional Heating of Total Hip Implants. Part 1: Measurements in Patients," Journal of Biomechanics, vol. 34, Issue 4, Apr. 2001, pp. 421-428.

(56) References Cited

OTHER PUBLICATIONS

Rohlmann, et al., "In vitro load measurement using an instrumented spinal fixation device", Medical Engineering & Physics, vol. 18, Issue 6, Sep. 1996, pp. 485-488.
Burny, et al., "Concept, design and fabrication of smart orthopaedic implants", Medical Engineering & Physics, 22 (2000), pp. 469-479.
Townsend, et al., "Remotely powered multichannel microprocessor based telemetry systems for smart implantable devices and smart structures," Proc. SPIE vol. 3673, pp. 150-156 (Mar. 1999).
D'Lima, et al., "An implantable telemetry device to measure intra-articular tibial forces", J Biomech. Feb. 2005; 38(2): pp. 299-304.
Bergmann, et al., "Hip Joint Contact Forces during Stumbling", Langenbecks Arch Surg. Feb. 2004; 389(1): 53-9. Epub Nov. 19, 2003.
Stansfield, et al., "Direct comparison of calculated hip joint contact forces with those measured using instrumented implants . . . " J Biomech. Jul. 2003;36(7):929-36.
Heller, et al., "Musculo-skeletal loading conditions at the hip during walking and stair climbing", J Biomech. Jul. 2001; 34(7):883-93.
Bergmann, et al., "Hip Contact Forces and Gait Patterns from Routing Activities", J. Biomech. Jul. 2001;34(7):859-71.
Bergmann, et al., "Frictional Heating of Total Hip Implants. Part 2: Finite Element Study," J Biomech. Apr. 2001;34(4):429-35.
Park, et al, "Hip muscle co-contraction: evidence from concurrent in vivo pressure measurement and force estimation", Gait Posture. Dec. 1999;10(3):211-22.
Graichen, et al., "Hip endoprosthesis for in vivo measurement of joint force and temperature", J Biomech Oct. 1999; 32(10):1113-7.
Krebs, et al., "Hip Biomechanics during Gait", J Orthop & Sports Phys Ther. Jul. 1998; 28(1):51-9.
Tackson, et al., "Acetabular pressures during hip arthritis exercises", Arthritis Care & Res. Oct. 1997;10(5):308-19.
Kotzar, et al, "Torsional loads in the early postoperative period following total hip replacement", J Orthop Res. Nov. 1995;13(6):945-55.
Bergmann, et al., "Is staircase walking a risk for the fixation of hip implants?," J Biomech, May 1995; 28(5):535-53.
Brand, et al, "Comparison of hip force calculations and measurements in the same patient", J Arthroplasty, Feb. 1994; 9(1):45-51.
Bergmann, et al., "Hip joint loading during walking and running, measured in two patients", J Biomech, Aug. 1993;26(8):969-90.
Graichen, et al., "Four-channel telemetry system for in vivo measurement of hip joint forces", J Sioment Eng, Sep. 1991;13(5):370-4.
Kotzar, et al., "Telemeterized in vivo hip joint force data: a report on two patients after total hip surgery", J Orthop Res., Sep. 1991, 9(5):621-33.
Morrell, et al., "Corroboration of in vivo cartilage pressures with implacations for synovial joint tribology and . . . ", Proc Natl Acad Sci USA, Oct. 11, 2005; 102(41 ):14819-24.
McGibbon, et al., "Cartilage degeneration in relation to repetitive pressure: case study of a unilateral hip hemiarthroplasty patient". J Arthroplasty, Jan. 14, 1999(1):52-8.
Lu, et al., "Influence of muscle activity on the forces in the femur: An in vivo study", J Biomech, Nov.-Dec. 1997;30(11-12):1101-6.
Taylor, et al., "Telemetry of forces from proximal femoral replacements and relevance to fixation", J Biomech, Mar. 1997;30(3):225-34.
Puers, et al., "A telemetry system for the detection of hip prosthesis loosening by vibration analysis", Sensors and Actuators 85 (2000) 42-47.
Aminian K, et al., "Temporal Feature Estimation During Walking Using Miniature Accelerometers . . ." Med Biol Eng Comput, 1999, 37, 686-691.
Bussmann JBJ, et al., "Analysis and Decomposition of Signals Obtained by Thigh-Fixed Uni-Axial Accelerometry During Normal Walking," Med Biol Eng Comput, 2000, 38, 632-638.
Petrofsky JS, et al., "Joint Acceleration during Gait in Relation to Age," Eur J Appl Physiology. 2004, 92: 254-262.
Patent Application for U.S. Appl. No. 60/710,550, filed Aug. 23, 2005.

International Search Report for International Application PCT/US2005/040052 dated Jun. 22, 2006, 8 pages.
Written Opinion of the International Search Authority issued in PCT/US2005/040052 on May 20, 2006, 9 pages.
International Preliminary Report on Patentability issued in PCT/US2005/040052 on May 8, 2007, 10 pages.
International Search Report for International Application PCT/US2006/033326 dated Dec. 13, 2006, 5 pages.
International Search Report and Written Opinion for International Application PCT/US2007/062757 dated Nov. 19, 2007, 8 pages.
International Search Report for International Application PCT/US2008/075316 dated Dec. 3, 2008, 2 pages.
International Search Report for International Application PCT/US2008/032540 dated Apr. 29, 2009, 3 pages.
International Preliminary Report on Patentability for International Application No. PCT/US2007/062757, mailed Aug. 26, 2009, 6 pages.
International Preliminary Report on Patentability for International Application No. PCT/US2008/075316, mailed Mar. 9, 2010, 7 pages.
Bergmann, et al, "Design and Calibration of Load Sensing Orthopaedic Implants," Journal of Biomechanical Engineering, Apr. 2008, vol. 130, 9 pages.
Catrysse, M., et al., "An Inductive Powering System with Integrated Bidirectional Datatransmission," Sensors and Actuators A: Physical, vol. 115, Issues 2-3, Sep. 21, 2004, pp. 221-229, The 17th European Conference on Solid-State Transducers.
Claes, L.E., and Cunningham, J.L., "Monitoring the Mechanical Properties of Healing Bone," Clin Orthop Relat res (2009) 467:1964-1971.
Kao-Shang Shih, et al, "Influence of Muscular Contractions on the Stress Analysis of Distal Femoral Interlocking Nailing," Clinical Biomechanics, 23 (2008) 38-44.
Westerhoff, P., "An Instrumented Implant for in vivo Measurement of Contact Forcdes and Contact Moments in the Shoulder Joint," Medical Engineering & Physics, 31 (2009) 207-213.
Swedberg, Claire, "Surgeon Designs System to Monitor Orthopaedic Implants and Promote Healing," RFID Journal, reprinted from http://www.rfidjournal.com/article/articleprint/3978/-1/1 on Mar. 26, 2008, 2 pages.
Rapp, Susan M., "Smart Implants to Provide Feedback, Measure Joint Loads, Detect Infection," Orthopedics Today, 2008, reprinted from http://www.orthosupersite.com/view.asp?rID=28657 on Jun. 6, 2008, 3 pages.
Seide, K., et al., "An Intelligent Internal Fixator System for Long Bones," 52nd Annual Meeting of the Orthopaedic Research Society, Paper No. 1698.
Rorie, J.F., et al, "A Telemetric Instrumentation System for Orthopaedic Implants," Apr. 19, 1995, 15 pages.
Arms, S.W., et al., "Wireless Strain Measurement Systems - Applications and Solutions," presented at NSF-ESF Joint Conference on Structural Health Monitoring, Strasbourg, France, Oct. 3-5, 2003.
Yang, G.Y., et al, "Design of Microfabricated Strain Gauge Array to Monitor Bone Deformation in Vitro and in Vivo," Proceedings of the Fourth IEEE Symposium on Bioinformatics and Bioengineering, May 19-21, 2004, 8 pages.
Einhorn, T.A., "The Cell and Molecular Biology of Fracture Healing," Clin Orthop, 1998: Suppl: 355:7-21.
Elvin, N., et al., "A Self-Powered Mechanical Strain Energy Sensor," Smart Matter Struct 2001; 10:1-7.
Kummer, F. J., et al., "Development of a Telemeterized Should Prosthesis," Clin Orthop Relat Res., Sep. 1996(330):31-4.
Morris BA, D'lima, D.D , J., Kovacevic, N., Arms, S.W., Townsend, C.P., and Colwell, C.W. Jr., "e-Knee: Evolution of the Electronic Knee Prosthesis," J Bone Joint Surg., 83:62-66, 2000.
Kaufman, K., Irby, S.E., and Colwell, C.W., "Instrumented Implant for Measuring Tibiofemoral Forces," J. Biomechanics, 29:667-671, 1996.
Taylor, S.J.G., Walker, P.S., Perry, J.S., Cannon, S.R., and Woledge, R., "The Forces in the Distal Femur and the Knee During Walking and Other Activities Measured by Telemetry," The Journal of Arthroplasty, 13:428-437, 1998.

(56) References Cited

OTHER PUBLICATIONS

SRI Consulting, "RFID Technologies", 2004; and Silicon Chip Online, "RFID Tags—How They Work." reprinted from http://www.siliconchip.com.au/cms/A30750/article.html.
Global market for RFID in healthcare 2006-2016 by value: Source: IDTechEx, RFID in Healthcare 2006-2016.
Healthcare RFID Medical Microchip, Yenra, Apr. 30, 2003, reprinted from http://www.yenra.com/healthcare-rfid-medical-microchip/.
Verichip System, Product of VeriChip Corp., reprinted from http://www.verichipcorp.com/content/solutions/verichip reprinted on Apr. 26, 2011.
Sub-dermal RFID, Yenra, Sep. 25, 2003, reprinted from http://www.yenra.com/subdermalrfid/.
Clyde Church, "Radio Frequency Identification (RFID) Tracking of Orthopaedic Inventories Fact or Fiction, Today and Tomorrow," BONE Zone, Spring 2004, pp. 35-40.
Luis Figarella, Kirk Kikirekov, Heinrich Oehlmann, Radio Frequency Identification (RFID) in Health Care, Benefits, Limitations, Recommendations, A Health Industry Business Communications Council HIBCC White Paper (2006).
Alex Macario; Dean Morris; Sharon Morris "Initial Clinical Evaluation of a Handheld Device for Detecting Retained Surgical Gauze Sponges Using Radiofrequency Identification Technology" Arch Surg., 2006; 141:659-662.
Patricia Kaeding "RFID medical devices—Opportunities and challenges," Published Oct. 19, 2005, Wisconsin Technology Network, http://wistechnology.com.
Communication pursuant to Article 94(3) EPC for EPO Application No. 07717657.6, mailed Jul. 12, 2011, 4 pages.
First Office Action for Chinese Application No. 200680038574.1, mailed Oct. 9, 2009, 16 pages.
Second Office Action for Chinese Application No. 200680038574.1, mailed Jul. 7, 2011, 8 pages.
Final Office Action for U.S. Appl. No. 12/528,243, mailed Jan. 24, 2012, 11 pages.
Japanese Notice of Reasons for Rejection for Application No. 2008-528223 mailed Nov. 1, 2011 (English translation), 3 pages.
Chinese Decision on Rejection for Chinese Patent Application 200680038574.1 issued Oct. 26, 2011 (English translation), 12 pages.
International Preliminary Report on Patentable for International Application No. PCT/US2006/033326, dated Feb. 26, 2008, 9 pages.
Written Opinion of the International Search Authority for International Application PCT/US2006/033326, mailed Feb. 23, 2008, 8 pages.
International Preliminary Report on Patentability for International Application No. PCT/US2009/032540, dated Aug. 3, 2010, 5 pages.
Written Opinion of the International Search Authority for International Application PCT/US2009/032540, dated Aug. 1, 2010, 4 pages.
Written Opinion of the International Search Authority for International Application PCT/US2008/075316, dated Mar. 6, 2010, 6 pages.
Office Action for U.S. Appl. No. 12/528,243, mailed Jun. 23, 2011, 10 pages.
Notice of Allowance for U.S. Appl. No. 12/064,546, mailed Dec. 27, 2011, 8 pages.
Office Action for U.S. Appl. No. 11/718,588, mailed Dec. 8, 2010, 9 pages.
Final Office Action for U.S. Appl. No. 11/718,588, mailed May 5, 2011, 16 pages.
Office Action for U.S. Appl. No. 11/718,588, mailed Dec. 15, 2011, 17 pages.
International Search Report for International Application PCT/US2009/032540 dated Apr. 29, 2009, 3 pages.
Global market for RFID in healthcare 2006-2016 by value: Source: IDTechEx, RFID in Healthcare 2006-2016, May 1, 2006.
Office Action for U.S. Appl. No. 12/528,243, mailed May 11, 2012.
Office Action for U.S. Appl. No. 11/718,588, mailed Jul. 16, 2012.
Decision of Rejection for Japanese Application 2008-528223, mailed Jul. 24, 2012.
First Office Action for Chinese Application No. 200880115437.2, mailed Nov. 22, 2012.
Office Action for Chinese Application No. 200980112399, mailed Dec. 25, 2012.
Patent Examination Report No. 1 for Australian Application No. 2009209045, mailed Nov. 29, 2012.
Office Action for U.S. Appl. No. 12/865,657, mailed Jan. 23, 2013.
Office Action for U.S. Appl. No. 12/528,243, mailed Dec. 19, 2012.
Official Inquiry for Japanese Application No. 2012-23327, mailed Apr. 9, 2013.
Notice of Reexamination for Chinese Application No. 200680038574.1, mailed Mar. 12, 2013.
Official Inquiry for Japanese Application No. 2008-528223, mailed Apr. 9, 2013.
Notice of Reasons for Rejection for Japanese Application No. 2010-545186, mailed May 28, 2013.

* cited by examiner

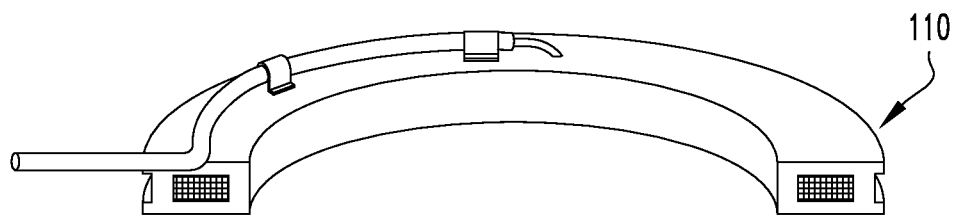
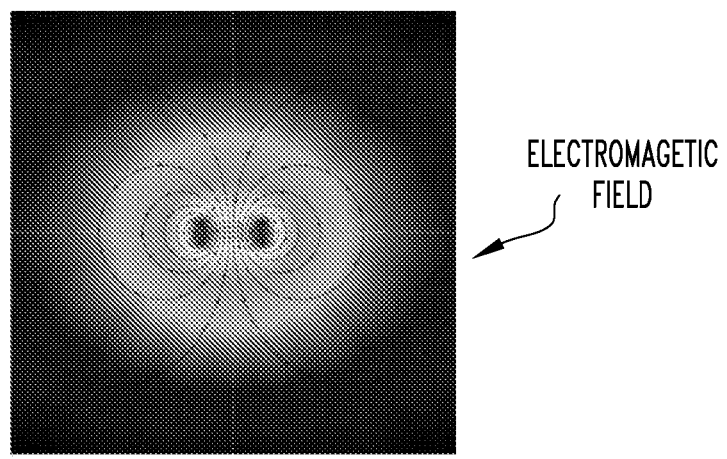
ELECTROMAGETIC FIELD
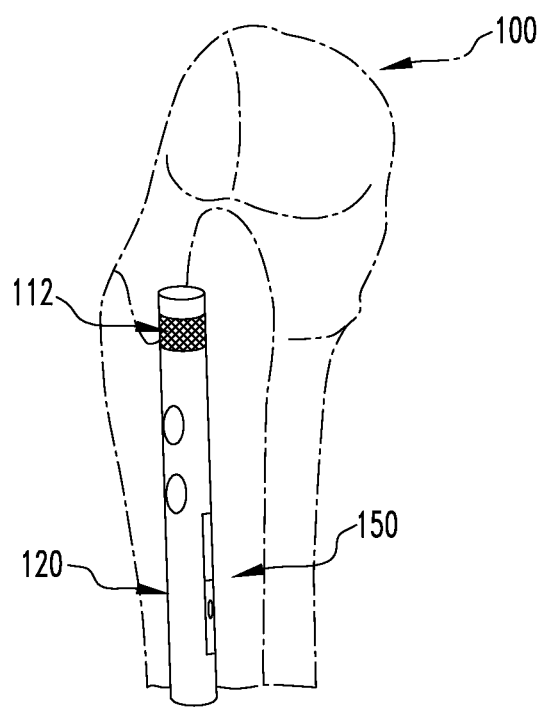
FIG.10

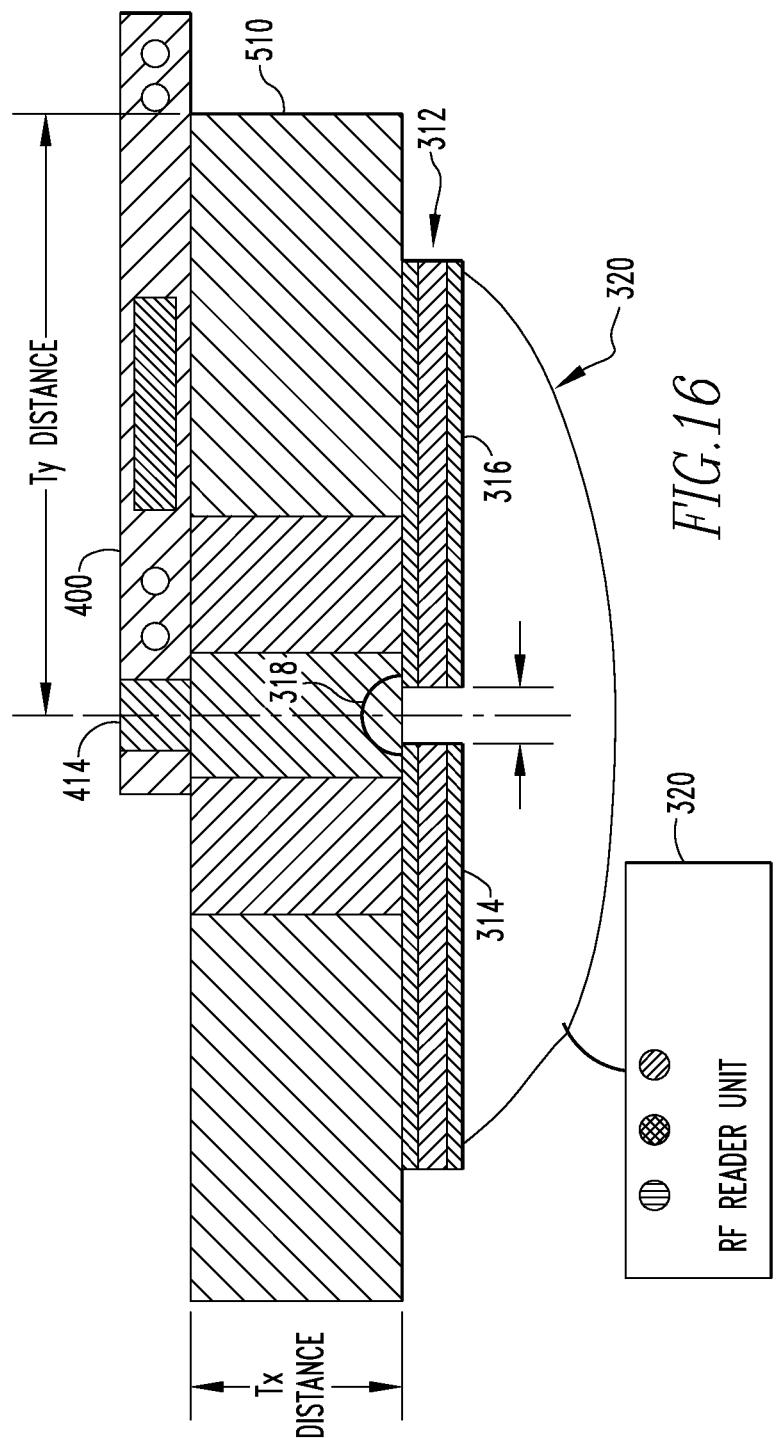

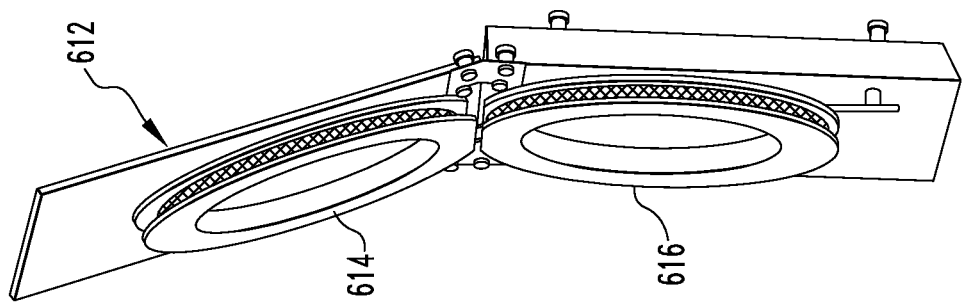
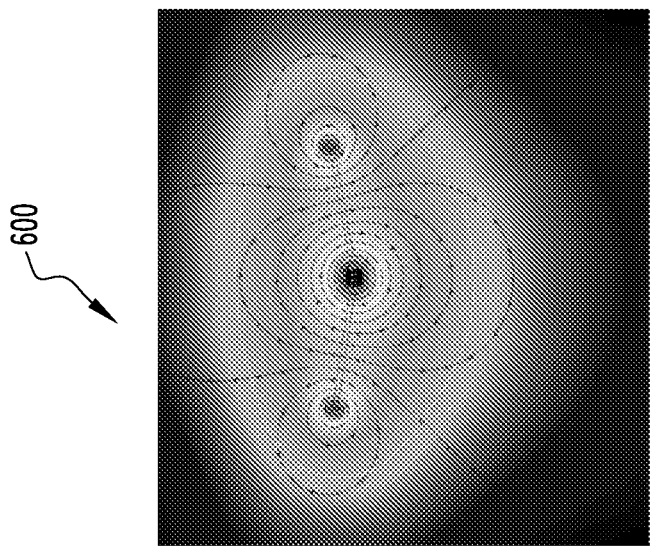
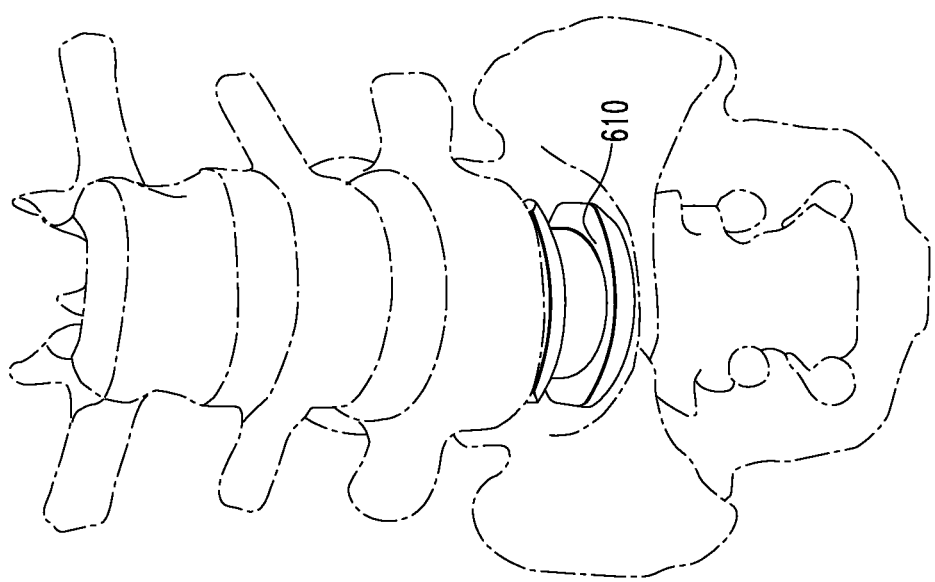
FIG. 18

SYSTEM AND METHOD FOR COMMUNICATING WITH A TELEMETRIC IMPLANT

CROSS-REFERENCE TO RELATED APPLICATIONS

This application is a National Phase of International Application No. PCT/US2008/075316, filed 5 Sep. 2008 which claims priority to U.S. Provisional Application Ser. No. 60/970,460, filed on 6 Sep. 2007. Each prior application is incorporated by reference herein.

BACKGROUND OF THE INVENTION

1. Field of the Invention

The present invention relates generally to telemetric systems and more particularly to devices for adjusting the electromagnetic field of a telemetric system.

2. Related Art

Wireless technology in devices such as pagers and handheld instruments has long been exploited by the healthcare sector. However, skepticism of the risks associated with wireless power and communication systems has prevented widespread adoption, particularly in orthopaedic applications. Now, significant advances in microelectronics and performance have eroded many of these perceived risks to the point that wireless technology is a proven contender for high integrity medical systems. Today's medical devices face an increasingly demanding and competitive market. As performance targets within the sector continue to rise, new ways of increasing efficiency, productivity and usability are sought. Wireless technology allows for two-way communication or telemetry between implantable electronic devices and an external reader device and provides tangible and recognized benefits for medical products and is a key technology that few manufacturers are ignoring.

Telemetry systems typically comprise a single coil transmitter for transmitting electromagnetic signals and a receiver for receiving the electromagnetic signals from the transmitter. These coils are normally arranged in a parallel configuration. The telemetry data might be any physical measurement, such as implant load, implant micro-motion, alkalinity, temperature, pressure, etc., which is sensed by a remote telemetry unit.

Currently, Radio Frequency (RF) telemetry and inductive coupling systems are the most commonly used methods for transmitting power and electronic data between the implant and the companion reader. Radio telemetry system employs one of several different modulation methods and one of several different multiplexing techniques in order to transmit information produced by multiple sensors to a user's location remote from the sensors. Methods of modulating a carrier frequency to convey information include amplitude modulation, frequency modulation, phase modulation, and pulse modulation.

The short range of conventional telemetry devices is a potential limitation of telemetric implants for medical applications. In the medical monitoring field, continuously accessible telemetry over a longer range has been sought. Increased read range, however, has implications on the reader system in terms of power, size and cost. As best seen in FIG. 1, effective read range typically has a logarithmic relationship with power consumption. In the graph illustrated in FIG. 1, a read range of approximately 11 inches requires about 100 watts of power.

U.S. Pat. No. 5,630,835 discloses a telemetry receiver coil arrangement of the generic type mentioned above. The '835 Patent discloses an electronic apparatus for the non-invasive communication with a cardiac pacemaker. An antenna arrangement with two coils connected in opposite directions is provided in the electronic apparatus. This antenna arrangement with two coils connected in series in opposition of phase helps suppress the effects of so-called far-field interference signals on the received near-field signals from the implant.

U.S. Pat. No. 5,741,315 teaches, in a telemetric data transmission device, to dispose a receiver coil and a compensation coil of differing diameters on a cup-shaped support such that inhomogeneous signals—namely the signals emitted by the implant—are observed only in the receiver coil, whereas homogeneous signals—namely interference signals—are measured also in the compensation coil.

U.S. Pat. No. 6,405,088 relates to a telemetry coil arrangement for receiving data signals in particular from cardiologic implants, comprising a pair of coils disposed one after the other in the direction of reception.

There remains a need in the art for improved telemetry systems and particularly a need for devices to adjust the electromagnetic field of a telemetric system.

SUMMARY OF THE INVENTION

It is in view of the above problems that the present invention was developed. According to some aspects of the present invention, there may be provided a telemetric system. The telemetric system includes a telemetric implant, a reader unit adapted to read signals from the telemetric implant; and an antenna adapted for connection to the reader unit and to receive signals from the telemetric implant. The antenna includes a first coil, a second coil, and a connector. The first coil is electrically connected to the second coil, and the connector allows for movement of the first and second coils relative to each other.

In one embodiment of the invention, the first coil or the second coil is moved to shape the magnetic field produced by said coils.

In another embodiment of the invention, the first coil or the second coil is moved to conform the antenna to a mammalian tissue surface.

In yet another embodiment of the invention, the antenna is used to power and read the telemetric implant from an oblique angle.

In still another embodiment of the invention, the first coil and the second coil are housed in a flexible polymer.

In one embodiment of the invention, the first coil and the second coil are housed in a pouch.

In another embodiment of the invention, the system further includes a component selected from the group consisting of a computing device, a signal generator, a power supply, an audible feedback system, and a visual indicator.

In yet another embodiment of the invention, the system further includes at least one additional antenna coil.

In still another embodiment of the invention, the antenna further comprises at least one ferrite component.

In one embodiment of the invention, the reader unit comprises a microcontroller, a coil driver and reader, a frequency counter, and an amplifier, and wherein the telemetric implant comprises a power supply circuit, an oscillator circuit, and a load modulator circuit.

In another embodiment of the invention, the antenna sends radio-frequency power to the telemetric implant and receives data from the telemetric implant.

The invention has several features and advantages. For example, by careful consideration of the design of the reader device, it is possible to shape the magnetic field produced by the transmitter coils in order to improve the power transfer to an implant and decrease the effective reader range required to power the implant where the orientation of the implant is non-optimal for a single coil reader. The wireless flexible dual coil reader system described herein is simple to set up and use, offers "plug and play" performance, and can power and read data from an implant from either a parallel or an orthogonal position.

As another example, the dual coil reader system possesses the ability to power and read telemetric implants from an oblique angle. For example, a telemetric spinal implant (most notably in the lumbar region) where the internal receiver coil is difficult to couple with a conventional single transmitter coil arranged in a parallel configuration due to the distance between the implant and the reader. The coupling distance is significantly reduced when a dual coil reader is positioned on the back of the patient adjacent to the implant where the two sets of coils are arranged orthogonally.

Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

BRIEF DESCRIPTION OF THE DRAWINGS

The accompanying drawings, which are incorporated in and form a part of the specification, illustrate the embodiments of the present invention and together with the written description serve to explain the principles, characteristics, and features of the invention. In the drawings:

FIG. 10 illustrates the electromagnetic field simulation of a single coil;

FIG. 16 illustrates the telemetric system in a second embodiment;

FIG. 18 is a third embodiment of the telemetric implant.

DETAILED DESCRIPTION OF THE EMBODIMENTS

The following description of the depicted embodiment(s) is merely exemplary in nature and is in no way intended to limit the invention, its application, or uses.

Figure 1:
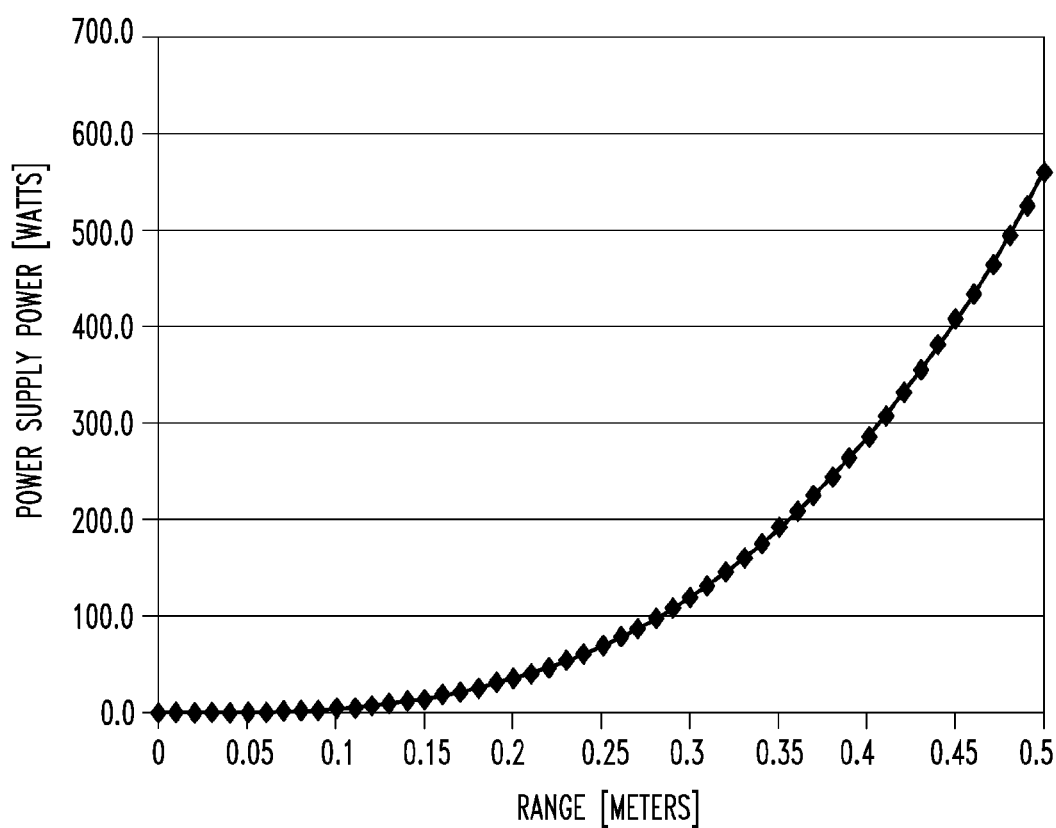
FIG. 1 is a graph illustrating a typical case of read range versus power supply power.
Figure 2:
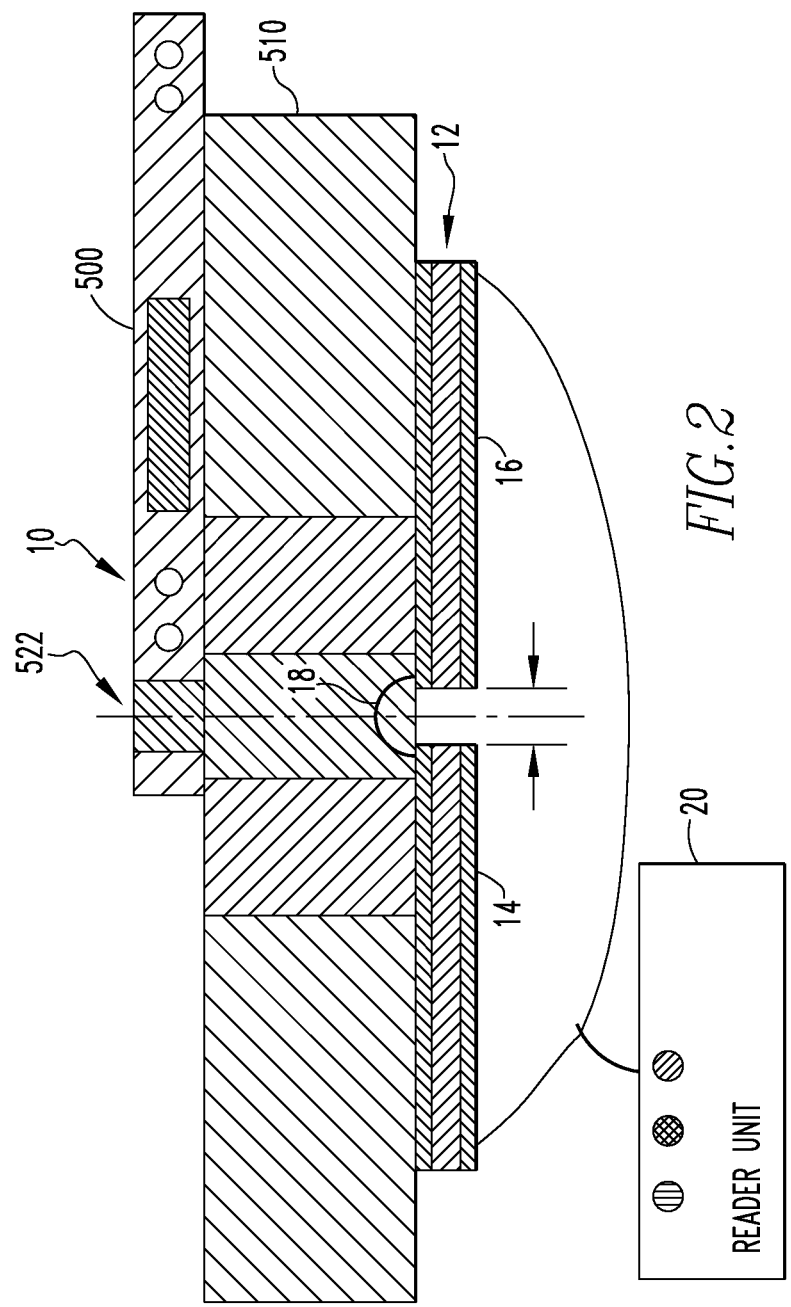
FIG. 2 is a schematic illustrating a first embodiment of a telemetric system.

FIG. 2 illustrates a telemetric system 10. The system 10 includes an antenna 12, a reader unit 20, and a telemetric implant 500. In the depicted embodiment, the telemetric implant 500 is an intramedullary nail, but other kinds and types of implants may be equally be used. As examples, the implant 500 may be a trauma orthopaedic implant, such as an intramedullary nail or a bone plate, or a prosthetic implant, such as a hip, a knee, or a shoulder implant. In the embodiment depicted in FIG. 2, the antenna 12 is resting upon tissue 510 that separates the antenna 12 and the implant 500. In general, the tissue 510 has a thickness of about 0.5 centimeters to about 10 centimeters.

The telemetric implant 500 may include one or more implant coils. Alternatively, the implant coils may be referred to as inductors. In the depicted embodiments, telemetric implant 500 has one implant coil 522. In FIG. 2, the implant coil 522 is formed by 600 turns of enameled copper wire having a diameter of about 0.1 mm. Of course, those skilled in the art would understand that these dimensions are merely exemplary and other dimensions may be used.

The antenna 12 includes a first coil 14, a second coil 16, and a connector 18. The connector 18 also may be termed a hinge. The first coil 14 is electrically connected to the second coil 16 in series in such a way that the magnetic fields generated by the first coil 14 and the second coil 16 are in anti-phase. The resulting magnetic field generated by the first coil 14 and the second coil 16 is such that magnetic field lines pass axially along the implant 500 in the region of the implant coil 522. The connector 18 physically connects the first coil 14 to the second coil 16. In the depicted embodiment, the connector 18 is flexible to allow movement of the coils 14, 16 relative to one another such that the antenna may conform to the surface of the tissue 510 during powering and data acquisition. Additionally, the flexibility of the connector 18 may provide for adjustment or alteration of the shape of the resultant magnetic field.

Figure 3A:
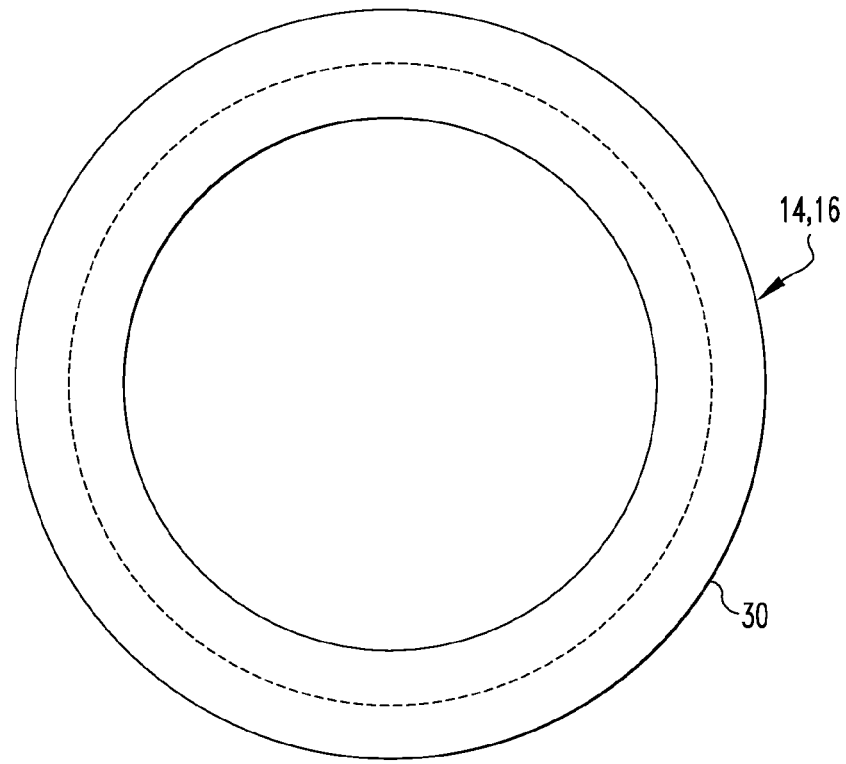
FIGS. 3A and 3B illustrate an antenna coil.
Figure 3B:

Coils 14, 16 may be of the same size and shape or the coils 14, 16 may be of different sizes. FIGS. 3A and 3B illustrate one particular embodiment of coils 14, 16. In FIGS. 3A and 3B, each coil 14, 16 is formed by a plastic spool 30 wound with conductive wire 32. In the depicted embodiment, at least 60 turns of copper wire having a diameter of about 0.4 mm is wound onto the plastic spool, and the plastic spool has an inner diameter of 100 mm, an outer diameter 140 mm, and a thickness of 8 mm thickness using a semi-automated coil winding machine. However, these dimensions are merely exemplary and those having ordinary skill in the art would understand that other dimensions might be used.

Figure 4:
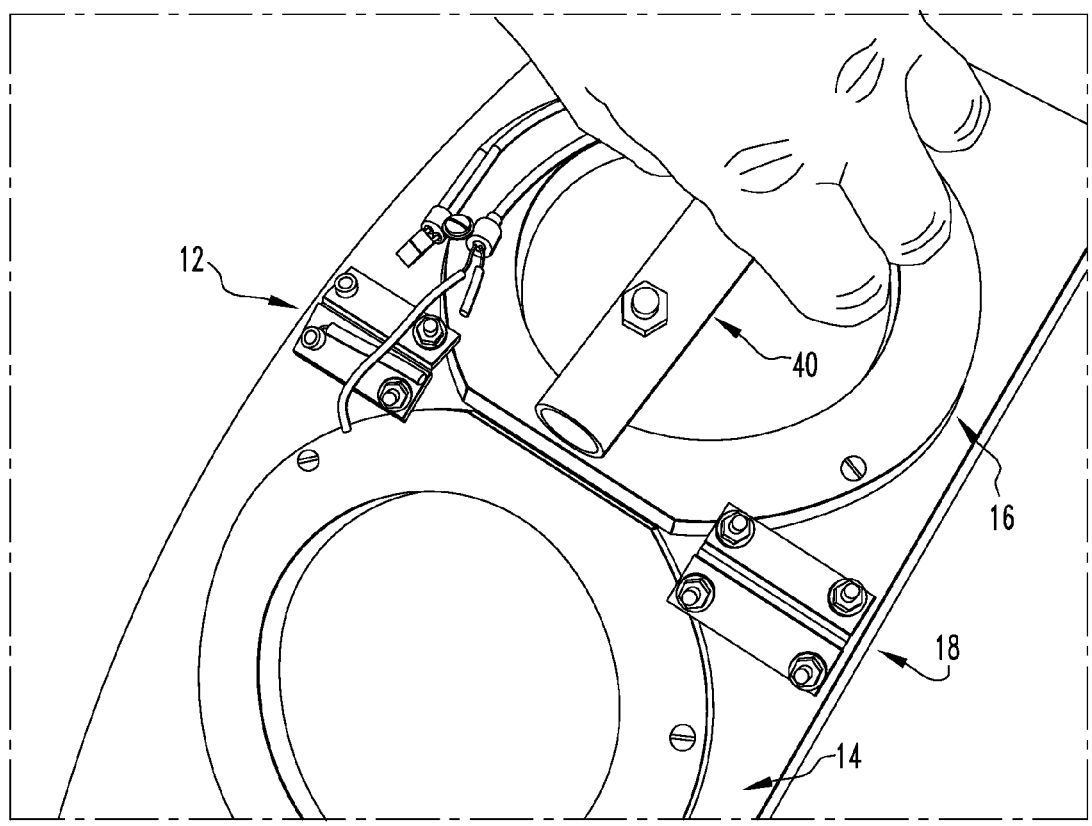
FIG. 4 is a picture of an antenna in a first embodiment.

FIG. 4 illustrates a first embodiment of the antenna 12. The coils 14, 16 are housed in a flexible polymer and are joined together in the middle using the hinge 18. The antenna 12 is equipped with a handle 40 that allows the device to be held by the user.

Figure 5B:
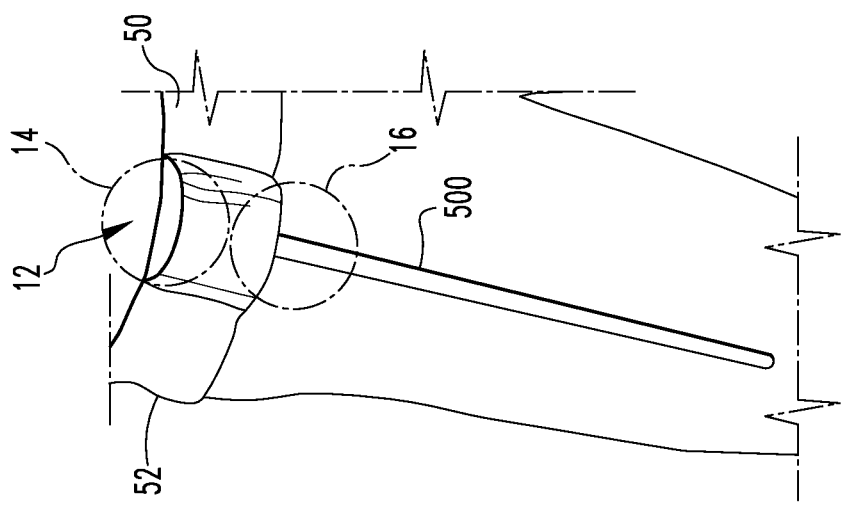
FIGS. 5A and 5B illustrate a second embodiment of the antenna.
Figure 5A:
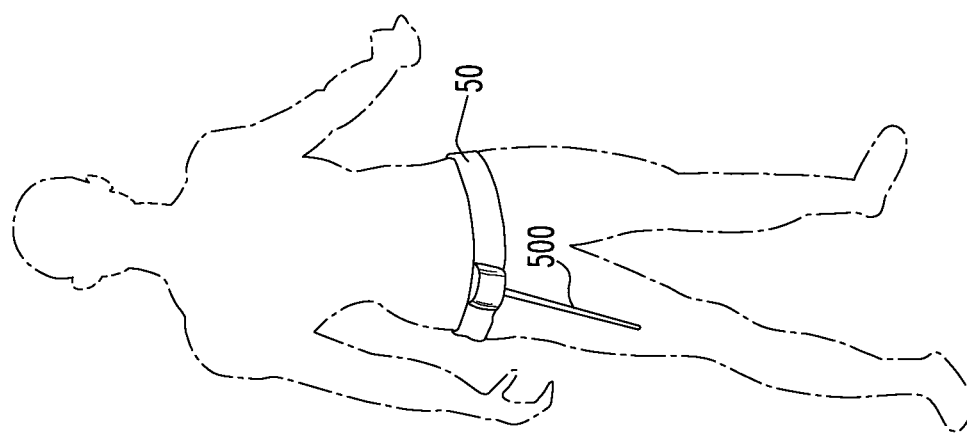

FIGS. 5A and 5B illustrate a second embodiment of the antenna 12. The coils 14, 16 are housed in a pouch 50 attached to a belt 52 that is worn around the patient's waist. The pouch 50 and the belt 52 give the patient more mobility during powering and data logging from the implant 500.

Figure 6:
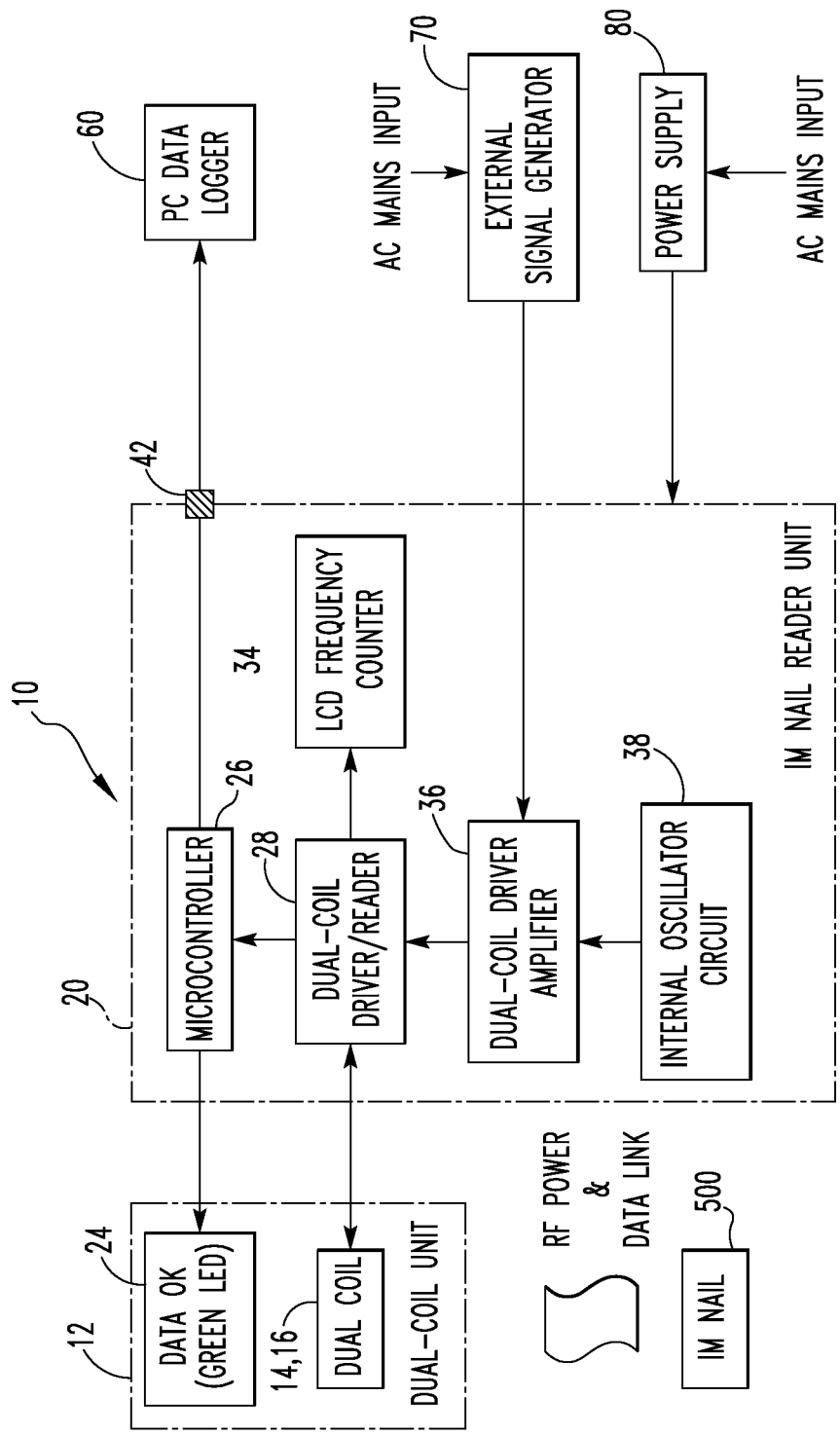
FIG. 6 is a block diagram illustrating the components of the telemetric system.

FIG. 6 illustrates a block diagram of the telemetric system 10. The system architecture includes a hand-held dual coil antenna 12, a reader unit 20, a computing device 60, a signal generator 70, and a power supply 80. Optionally, the system 10 may include an audible feedback system that informs the user when the implant is engaged and reliable data is being acquired. The antenna 12, which also may be termed a reader head, may be equipped with one or more signal "OK" light emitting diodes (LEDs) 24 to provide feedback to the user on optimizing the position of the reader relative to the implant 500. In an exemplary case, the signal "OK" LED 24 is illuminated when the implant frequency is between 5.3 kHz and 6.3 kHz and the signal is adequately received.

The reader unit 20 includes a microcontroller 26, a coil driver and reader 28, an LCD frequency counter 34, an amplifier 36, and a port 42. In the embodiment depicted in FIG. 6, the port 42 is an RS232 to PC connection point, but other types of connection ports may equally be used. In some embodiments, the signal generator 70 and the power supply 80 is integrated into the nail reader unit 20 formed by a single unit, such as a table-top unit. In one particular embodiment, the reader unit 20 includes an oscillator circuit 38, to optimize the drive frequency of the antenna 12 in order to maximize the power coupling to the telemetric implant 500. In the depicted embodiment, the drive frequency is optimized using phased loop techniques but other techniques may equally be used. These techniques may be particularly useful when the telemetric implant 500 is an intramedullary nail having a strain gauge electrically connected to an oscillator circuit, as is depicted in FIG. 8.

Figure 7:
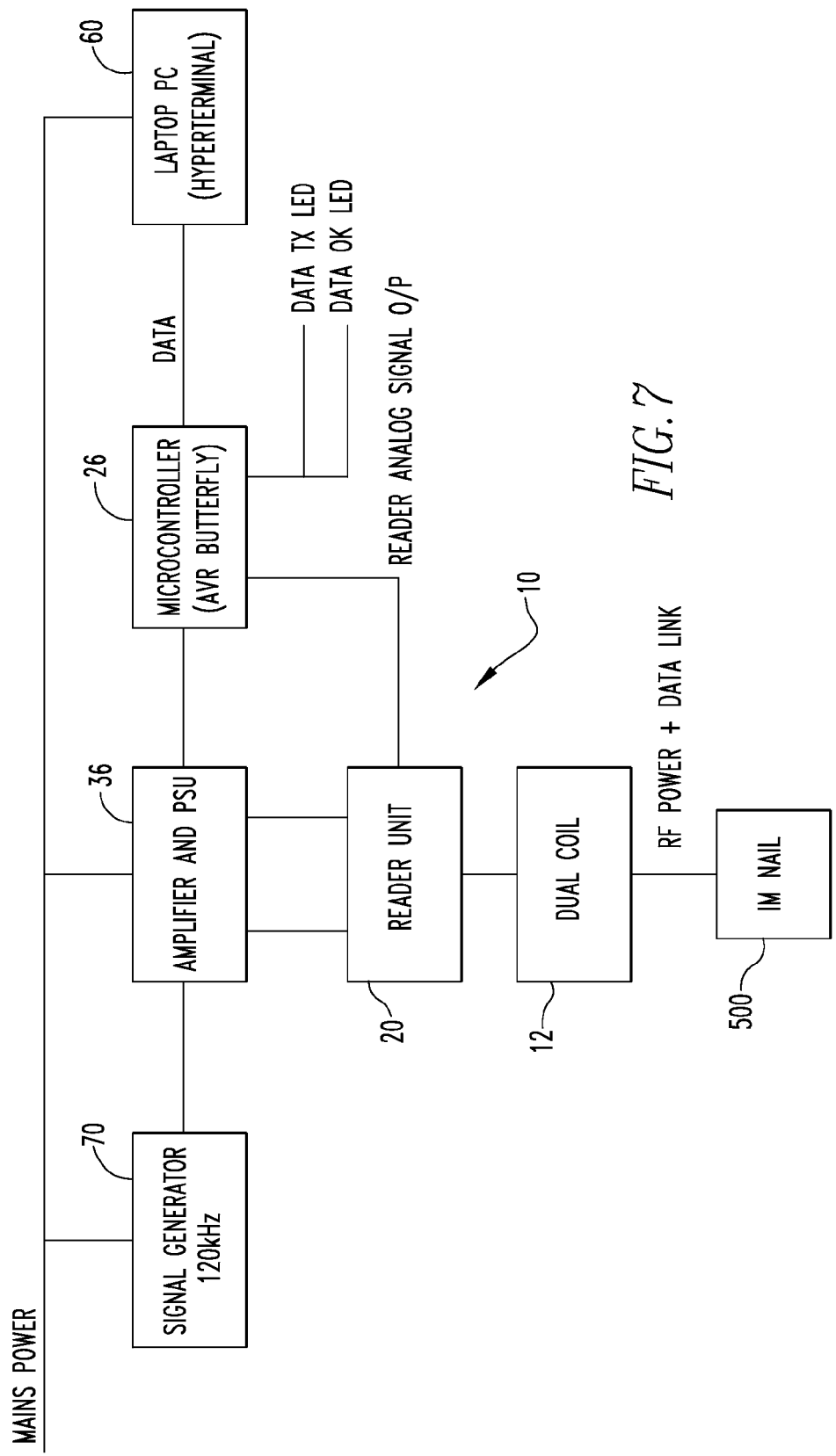
FIG. 7 is a block diagram illustrating power connections.

FIG. 7 is a schematic of the power connection for the system 10. System 10 includes the signal generator 70, the amplifier 36, the microcontroller 26, the computing device 60, the reader unit 20, the antenna 12, and the telemetric implant 500. The antenna 12 sends RF power to the telemetric implant 500 and receives data from the telemetric implant 500.

Figure 8:
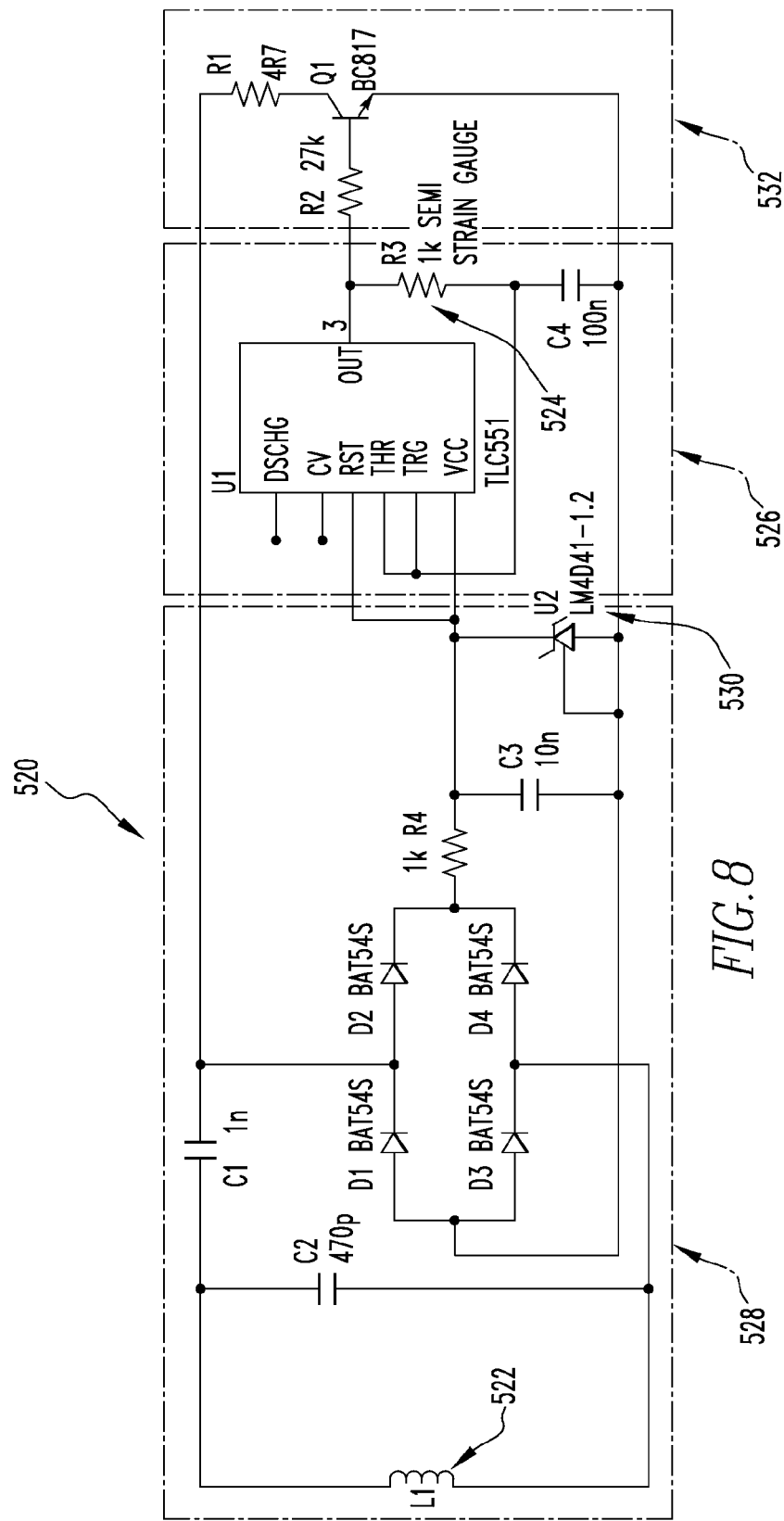
FIG. 8 is a circuit diagram of the telemetric implant.

FIG. 8 illustrates an exemplary schematic of on-board electronics 520 of the implant 500. In the depicted embodiment, the on-board electronics 520 includes a power supply circuit 528, an oscillator circuit 526, and a load modulator circuit 532. The power supply circuit 528 includes, among other things, the inductor or implant coil 522 and a voltage regulator 530. The oscillator circuit 526 includes, among other things, a strain gauge 524. In the depicted embodiment, the strain gauge is a micro-strain measuring gauge with product number KSP-2-1K-E4 from Kyowa Electronic Instruments Co., Ltd. and having an address of 3-5-1, Chofugaoka, Chofu, Tokyo 182-8520, Japan. Other strain gauges, however, may be used. Integrating the sensor into the oscillator circuit has the advantage of simplifying the instrumentation electronics. For example, a printed circuit board may be equipped with discrete components, simplifying the microcontroller interface, and allowing frequency measurements to be correlated with voltage measurements, which are in turn correlated with strain gauge measurements. The internal oscillator circuit aims to optimize the drive frequency of the antenna 12 in order to maximize the power coupling to the telemetric implant 500. In the depicted embodiment, the drive frequency is optimized using phased loop techniques but other techniques may equally be used. The on-board electronics 520 may take the form of a single chip and may eliminate the need for an external signal generator in the system 10.

Figure 9:
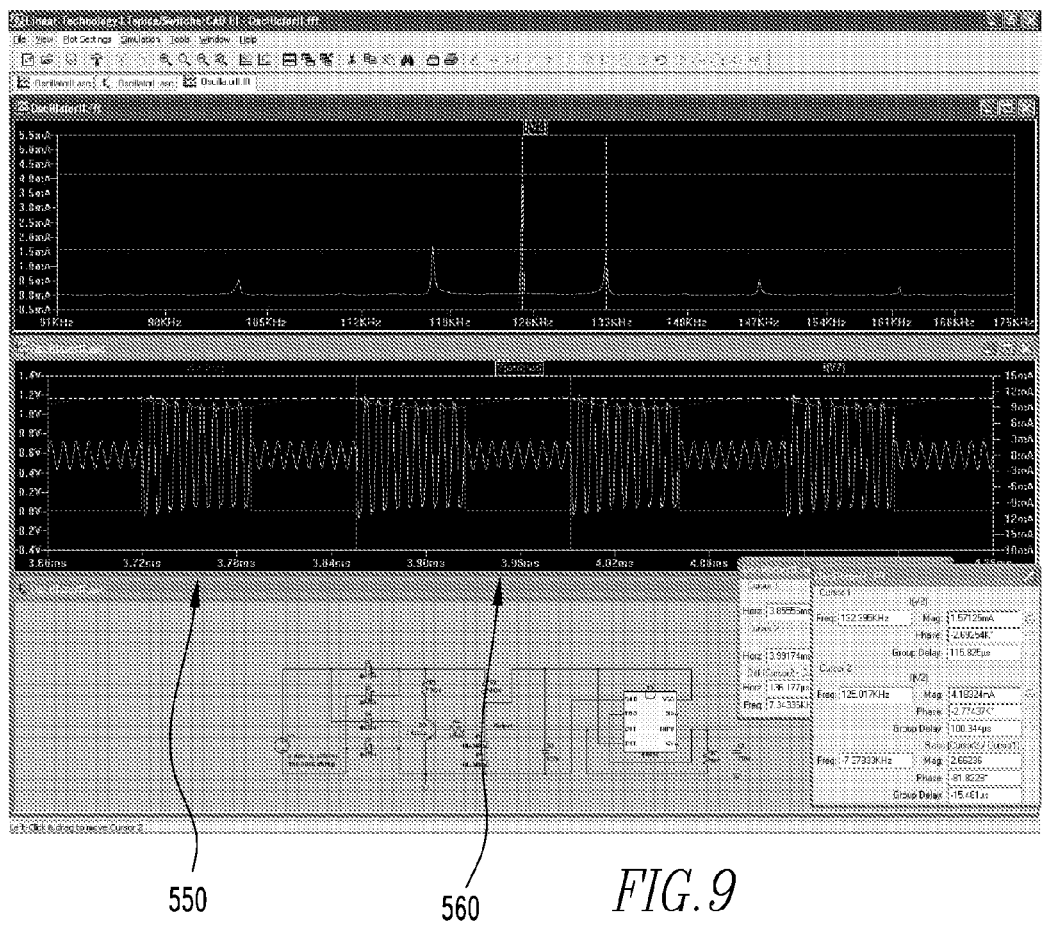
FIG. 9 illustrates the carrier wave and data wave.

The antenna 12 sends power to the on-board electronics 520, and the antenna 12 receives data from the on-board electronics 520. The inductor 522 receives a carrier signal 550 from the antenna 12 to inductively power the power supply circuit 528. In the embodiment depicted in FIG. 9, the carrier signal 550 has a frequency of about 125 kHz. The use of inductive power eliminates the requirement for a battery in the telemetric implant. In the depicted embodiment, the on-board electronics 520 operate only when powered inductively from the antenna 12. In other embodiments, a battery (not shown) or other power source may be used to power the on-board electronics 520 when not inductively powered. The on-board electronics 520 does not transmit raw data to the antenna 12 but instead modulates a load signal 560 via load modulator circuit 532. The load signal 560 is related to the amount of resistance measured by the strain gauge 524. In the depicted embodiment, the load signal 560 is modulated at a frequency between 5 kHz and 6 kHz but those skilled in the art would understand that other frequency bands may be used. The change in load on the telemetric implant 500 is transmitted by the antenna 12 and received by the reader 20.

FIG. 10 illustrates a system 100 having a single transmitter coil 110 arranged in parallel and on the same axis for maximum power coupling for a given separation with an internal receiver coil 112 of a telemetric implant 120 implanted in a bone 150. In the depicted embodiment, the telemetric implant 120 is an intramedullary nail, and the bone 150 is a femur. The transmitter coil 110 produces a magnetic field that is highly orientated in the direction between the receiver and transmitter coils. The coupling efficiency is significantly reduced when the coils are located greater than 10 centimeters apart. Further, the field generated from this particular coil arrangement is weak when the transmitter coil 110 is positioned perpendicular to the internal receiver coil 112. In other words, the coupling is reduced when the magnetic field lines are not well aligned with respect to the axis of the receiver coil.

In contrast to the system 100, if a plurality of transmitter coils are connected in anti-phase and arranged in series such that they are adjacent to one another and allowed to conform to the surface of the patient by positioning the coils orthogonally with respect to the implant coil or inductor 522, the magnetic field strength is relatively strong compared to the single coil arrangement. The increased field strength allows the telemetric implant to be powered and read from the lateral aspect of the tissue. This is significant as there has been a long felt but unresolved need in receiving telemetric implant signals through tissue.

Figure 11:
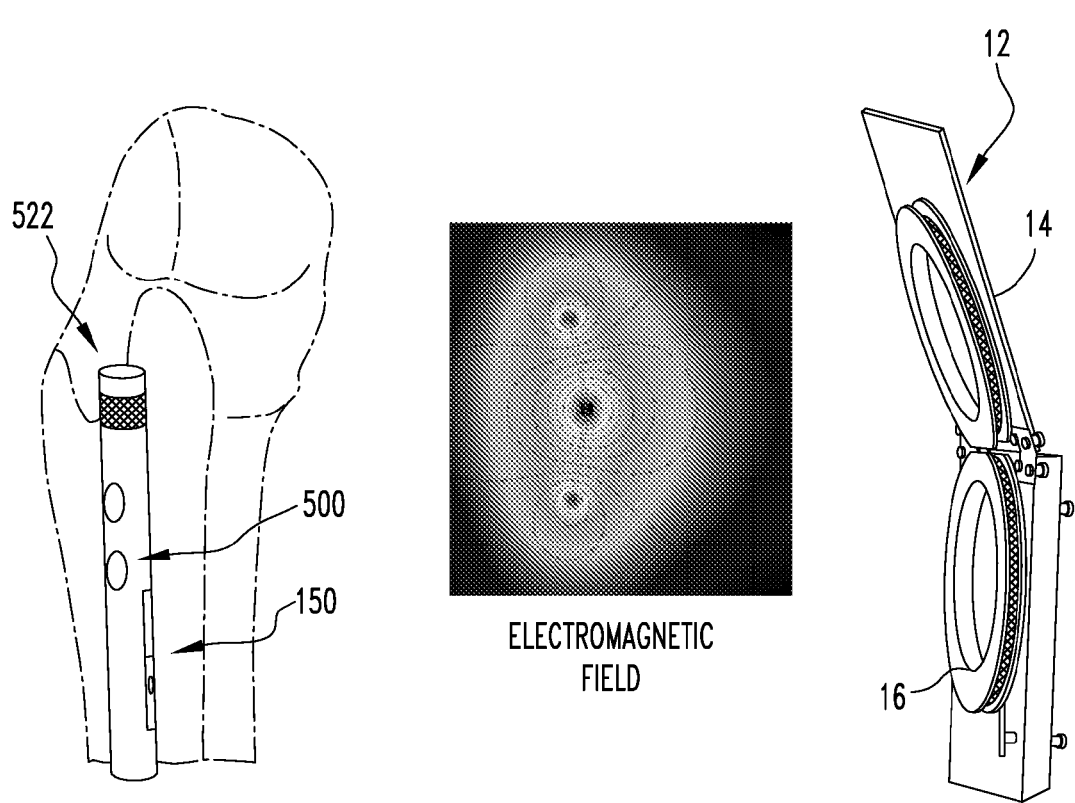
FIG. 11 illustrates the electromagnetic field simulation of an antenna having two coils.

FIG. 11 illustrates the antenna 12, the telemetric implant 500, and the bone 150. As noted above, the antenna 12 includes the coils 14, 16, and the telemetric implant 500 includes the inductor 522. The configuration or arrangement of the coils 14, 16 affects both the direction and strength of the magnetic field and coupling efficiency between the antenna 12 and the inductor 522. Altering the angle between the coils 14, 16 can focus the magnetic field generated by the dual coil arrangement.

Figure 12A:
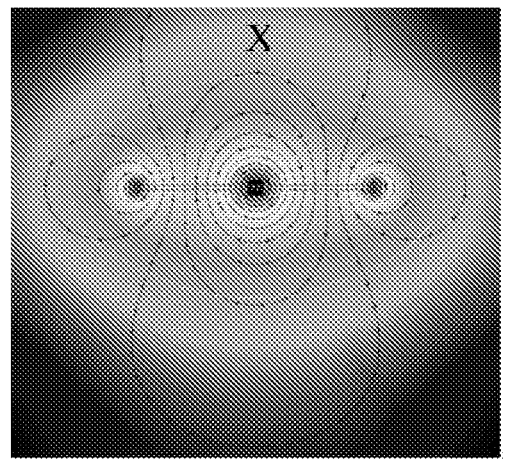
FIGS. 12A-12F illustrate electromagnetic field simulations for given antenna configurations.
Figure 12B:
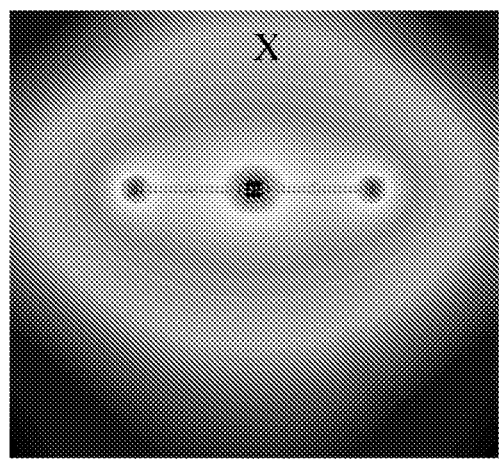
Figure 12C:
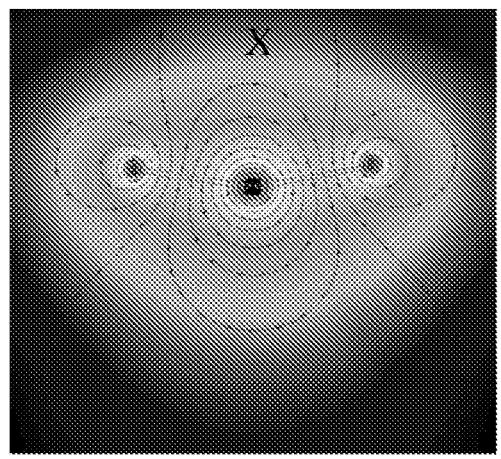
Figure 12D:
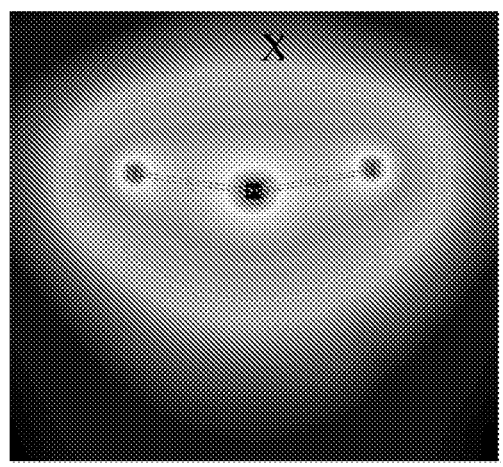
Figure 12E:
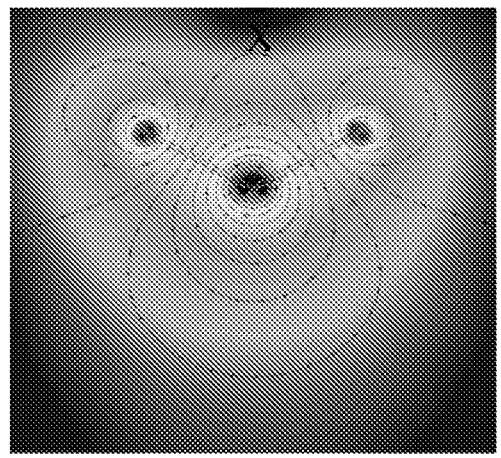
Figure 12F:
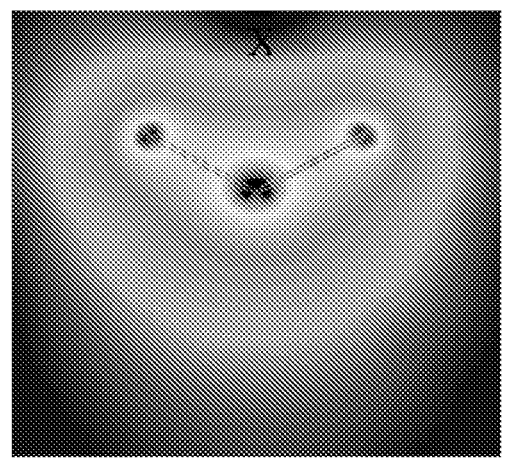

FIGS. 12A-12F illustrates the effect of coil angle on field strength. FIGS. 12A, 12C, and 12E illustrate resultant field lines and field strength, whereas FIGS. 12B, 12D, and 12F illustrate field strength only. In FIG. 12, "X" indicates the general position of the implant coil or inductor 522. By changing the angle between the first coil 14 and the second coil 16, the magnetic field can be manipulated. FIGS. 12A and 12B illustrate a resultant magnetic field strength when coils 14, 16 are generally planar with one another. When the coil is angle is decreased from 180 degrees to about 160 degrees, the magnetic-field appears to be better constrained in the region of the implant coil or inductor 522, as best seen in FIGS. 12C and 12D. In FIGS. 12E and 12F, the field becomes more focused when the coil angle is reduced from 160 degrees to 120 degrees. Moreover, field lines and field strengths are only slightly changed and still conform to the preferred coupling orientation for the implant. It is worth noting that these simulations do not take into account any effects of the magnetic field passing through living tissue.

In one particular embodiment, a coil angle of about 160 degrees is chosen to better follow the physical contours of an ovine hind limb in the vicinity of the hip producing a "flatter" magnetic field strength in the region of a telemetric intramedullary nail implant. This coil arrangement has been shown to improve coupling efficiency. Those skilled in the art would understand that the particular coil angle may be chosen based upon other factors and is not limited to specific coil angles or specific applications.

In some embodiments, the antenna further includes one or more components having ferrite attached to the handle side. As examples, the component having ferrite may take the form of an alloyed low-loss magnetic material or a composite structure. The ferrite component tightly constrains the magnetic field not utilized by the telemetric implant. The options for a component having ferrite may include: a single ferrite rod or plate mounted between the antenna coils; a series of parallel ferrite rods or plates mounted between the antenna coils; or a series of parallel ferrite rods or plates mounted between the antenna coils but with an air gap between the coils and the ferrite. The type and length of individual rods or plates may be selected to optimize magnetic-field coupling between the coils. The use of an air gap between the ferrite and the coils may allow for an increased range of coil angles. In the depicted embodiments, the ferrite takes the form of an iron rod or plate mounted to a plastic block. The component having ferrite also may be termed a ferrite former.

Figure 13:
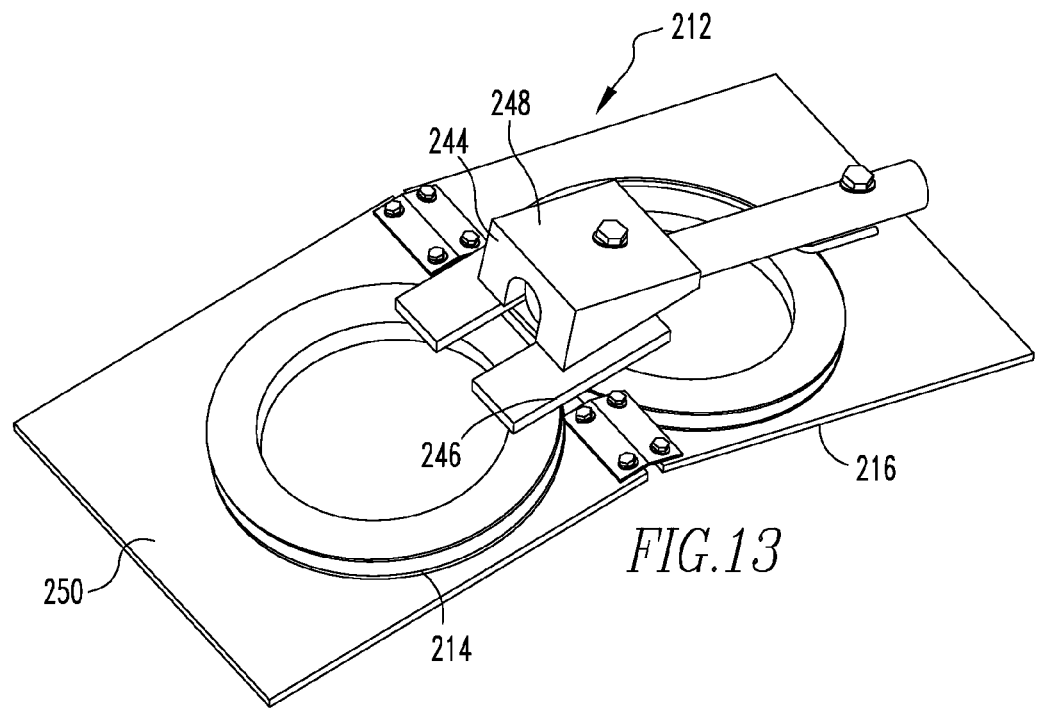
FIG. 13 illustrates an alternative embodiment of the antenna in a top view.
Figure 14:
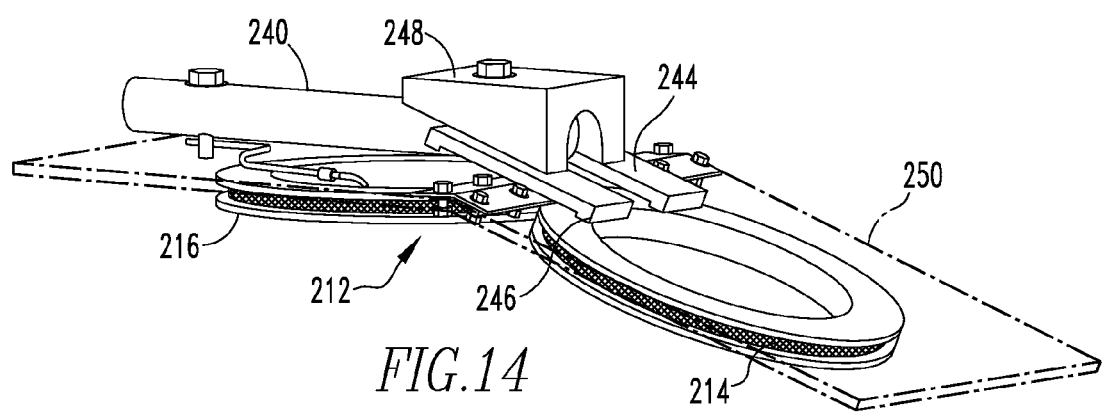
FIG. 14 illustrates an alternative embodiment of the antenna in a side view
Figure 15A:
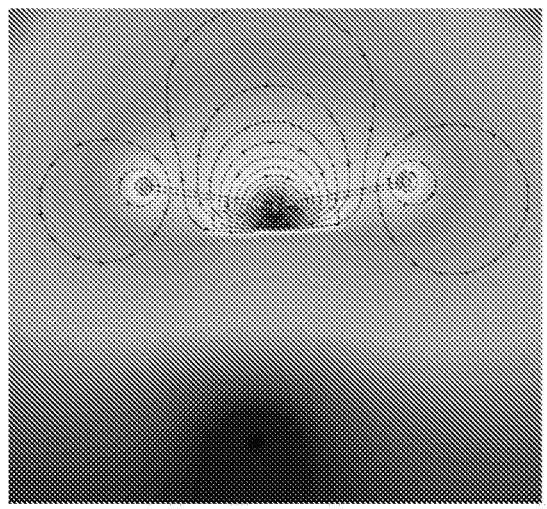
FIGS. 15A-15D illustrate electromagnetic field simulations for given antenna configurations.
Figure 15B:
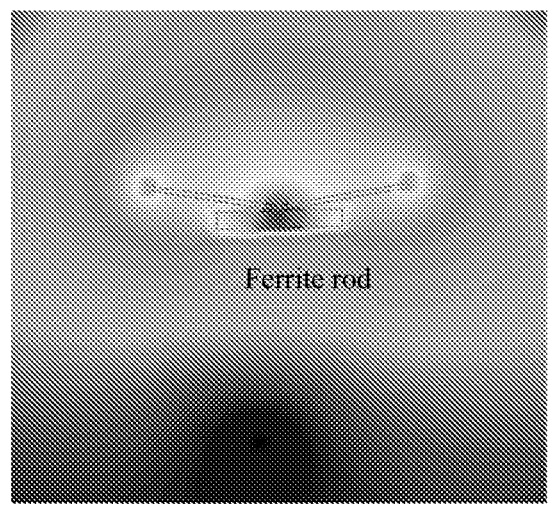
Figure 15C:
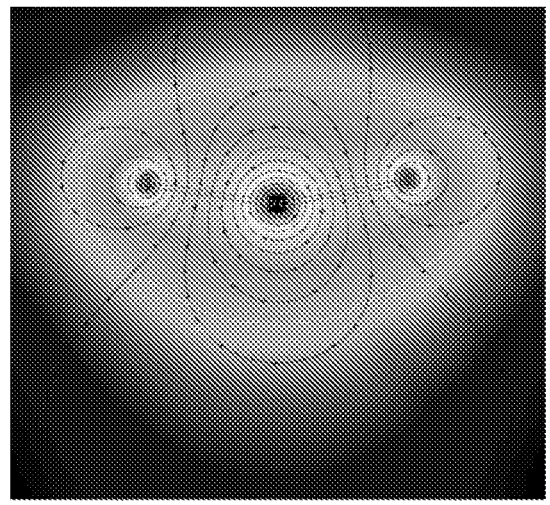
Figure 15D:
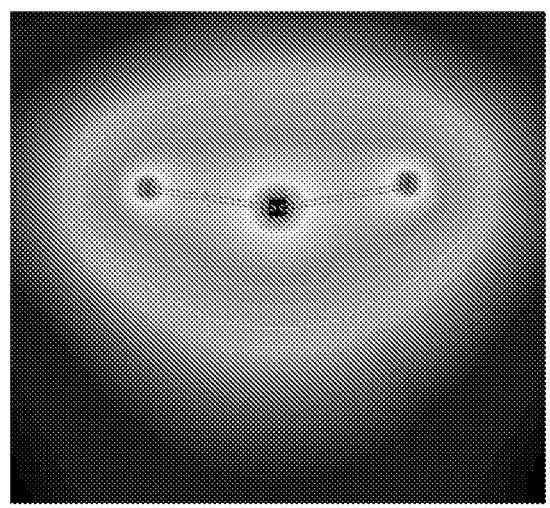

FIGS. 13 and 14 illustrate an antenna 212 having a first coil 214 and a second coil 216. The antenna 212 further includes at least one ferrite component. In the embodiment depicted in FIGS. 13 and 14, the antenna 212 includes a first ferrite forma 244 and a second ferrite forma 246. Those skilled in the art, however, would understand that a greater number or a fewer number of ferrite components may be used. In the embodiment depicted in FIGS. 13 and 14, the antenna 212 further includes a handle 240, a mounting block 248, and one or more mounting plates 250. In FIGS. 13 and 14, the mounting block 248 is plastic but other materials may be used. The mounting plate 250 merely provides some additional structural stability and may be omitted in some embodiments. In the embodiment depicted in FIGS. 13 and 14, the mounting plate 250 is made of clear plastic but other materials could equally be used.

The dimensions of the first ferrite forma 244 and the second ferrite forma 246 are approximately 75 mm×28 mm×6 mm in the depicted embodiments but those skilled in the art would understand that other dimensions and other shapes may be used. While the first ferrite forma 244 and the second ferrite forma 246 may be positioned equidistant over the center line between the coils 14, 16, those skilled in the art would understand that the position and/or dimension of the formas 244, 246 may be optimized to avoid saturation, to maximize coupling distance, to reduce coil power requirements, and/or to improve power coupling efficiency. In the embodiment depicted in FIGS. 13 and 14, the first ferrite forma 244, the second ferrite forma 246, and the handle 240 are mounted to the mounting block 248.

FIGS. 15A-D illustrate the effect of employing a ferrite component adjacent the coils 14, 16 in order to tightly constrain the magnetic field in the region not intended for the telemetric implant. In the embodiment depicted in FIGS. 15A-D, antenna 212 has a coil angle of 160 degrees and there are two ferrite components. Use of a low-loss ferrite material appears to constrain the magnetic field behind the coils 14, 16 whilst extending the magnetic field on the implant-side of the coils, enabling an increased coupling distance. In the embodiment depicted in FIGS. 15A-D, the addition of the ferrite components increased the coupling distance by about one centimeter, thereby providing a maximum coupling distance of about seven centimeters from about six centimeters without changing the power supplied to the coils 14, 16.

FIG. 16 illustrates a telemetric system 300. The system 300 includes an antenna 312, a reader unit 320, and a telemetric implant 400. The antenna 312 includes a first coil 314, a second coil 316, and a connector 318. The telemetric implant 400 includes an inductor or receiver coil 414. In the embodiment depicted in FIG. 16, the antenna 312 is resting upon tissue 510 that separates the antenna 312 and the implant 400.

The reader unit 320 is equipped with visual and audible indicators. In the embodiment depicted in FIG. 16, the visual indicators are light emitting diodes but other devices may equally be used. The visual and audible indicators enable the user to locate the optimum position for powering and reading the telemetric implant 400. The transverse distance between the antenna 312 and telemetric implant 400 in the lateral aspect of the tissue 510 is defined as Tx. Ty is defined as the longitudinal distance between the "sweet spot" located in the center of the antenna 312 and the center of the inductor 414. Within the so-called "sweet spot," the frequency of the oscillator circuit is constant but the amplitude is variable. Outside of the "sweet spot," the frequency changes and it is not recommended to acquire any meaningful measurements by the user. This can be controlled electronically using an onboard microcontroller removing the issue of human error.

In some embodiments, the reader unit 320 may be equipped with color-coded signals to indicate whether or not the antenna 312 is in an optimal position. For example, the reader unit 320 may be equipped with three color-coded light indicators. In the depicted embodiment, the reader unit 320 includes a red LED, an orange LED, and a green LED. Lighting of the red LED indicates that the antenna 312 is out of range. Lighting of the orange LED indicates that the antenna 312 is at least receiving some signals from the inductor 414. Lighting of the green LED indicates that the antenna 312 is in an optimal position to send power to the inductor 414 and receive signals from the telemetric implant 400. In some embodiments, a high pitch audible sound also informs the user that the implant 400 is powered and data can be read from the patient.

Figure 17A:
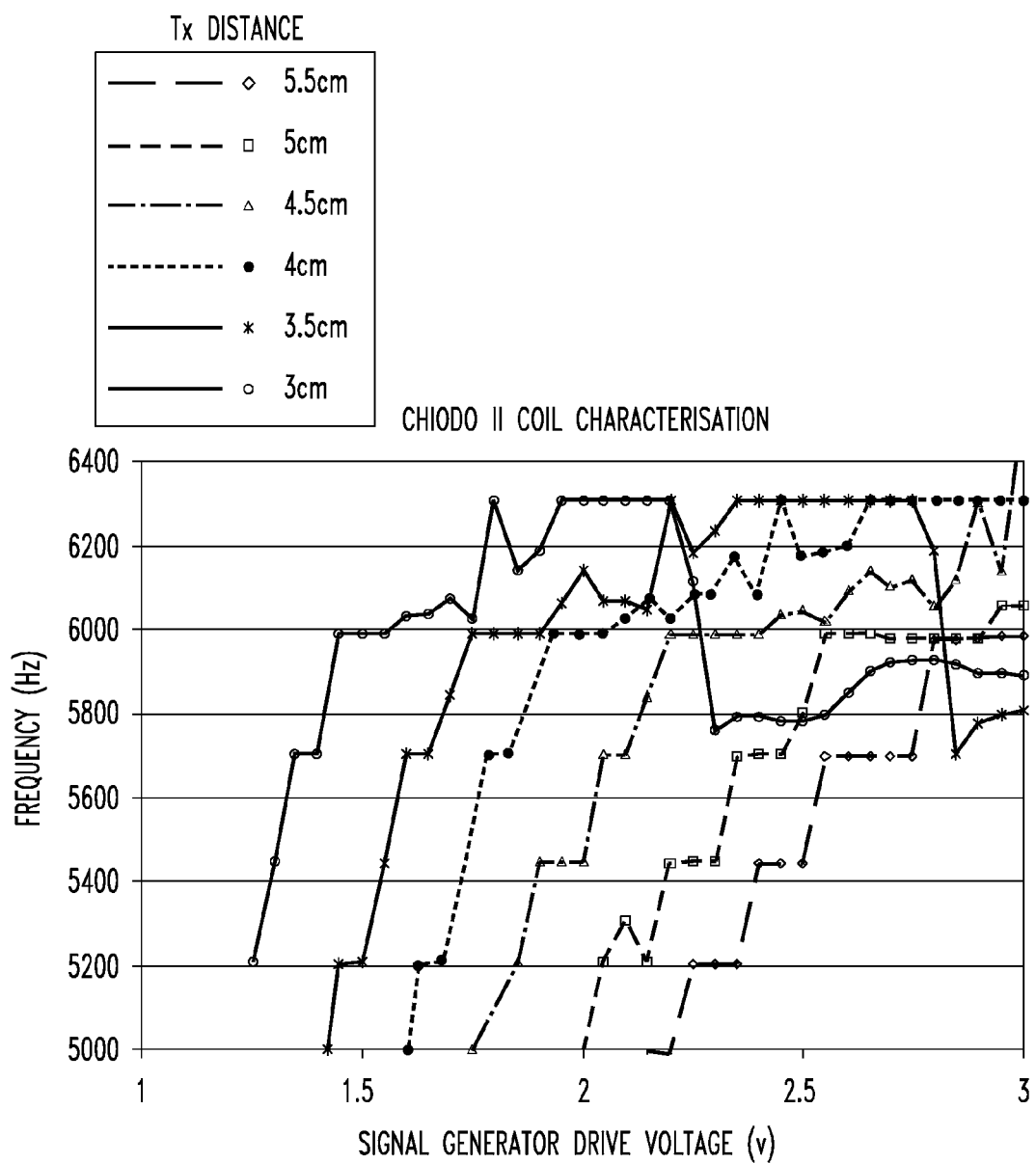
FIGS. 17A and 17B graphically illustrate signal generator drive voltage.
Figure 17B:
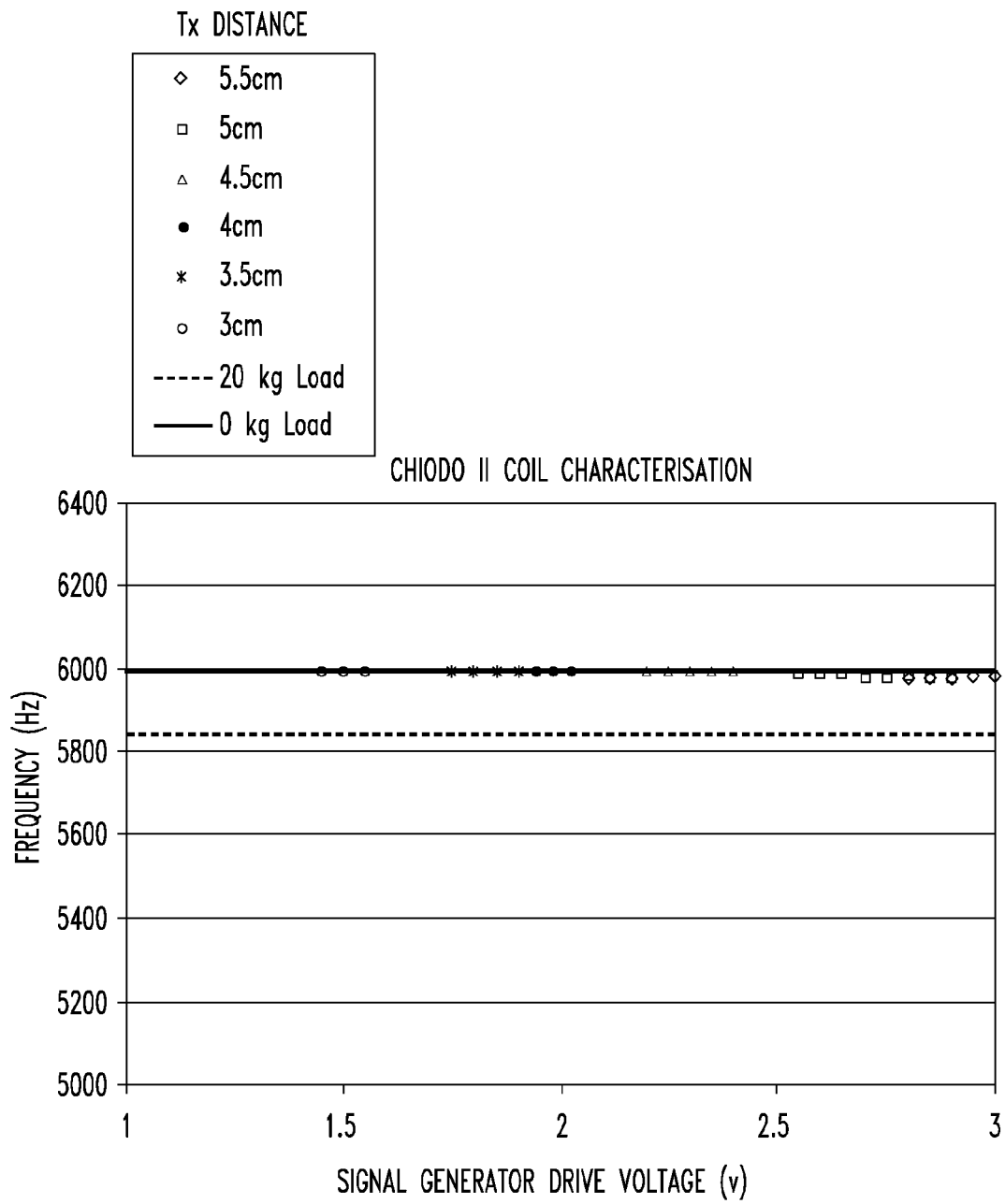

As best seen in FIG. 17A, Tx is internally compensated to match the tissue depth with the appropriate signal generator drive voltage (about 1 to about 3V). "Load on" and "load off" frequency responses, referred to as 6 kHz and 5.8 kHz respectively in FIG. 17B, as a function of tissue distance for a drive voltage between one and three volts. In the depicted embodiment, Tx is optimized at about five to about six centimeters for a drive voltage of about 2.5 volts. The diameter of the Ty "sweet spot" is about four centimeters.

FIG. 18 illustrates yet another alternative embodiment of the telemetric system 600. The system 600 includes, among other things, a telemetric implant 610 and an antenna 612. In the depicted embodiment, the telemetric implant 610 is a spinal implant placed in the lumbar region. The antenna 612 includes a first coil 614 and a second coil 616. Due to its configuration, the antenna 612 is capable of powering and reading the telemetric implant 610 from an oblique angle.

Increasing the magnetic field strength and hence coupling distance between the internal and external reader coils can be achieved by increasing the diameter of the coils and power output of the reader. The power coupling range also can be increased by taking measures to reduce induced eddy currents in the implant when the implant is manufactured from a conducting material, such as Ti64. This can be achieved by inserting notches, or slots, beneath the receiver coils wound onto the implant and filling the notches with a polymeric insulative material, such as epoxy resin.

Increasing the effective read range of the system also can be achieved by driving the embedded circuit in a pulsed or non-continuous manner. This embodiment may require additional circuitry to switch the strain gauge oscillator circuit 526 and load modulator circuit 532 on and off. Increasing or adding capacitance in the strain gauge circuitry may permit enough energy storage to get sufficient operation to read the signal. If the circuit is energized sufficiently to provide a signal for sufficient time to be read at least one time by the reader then the embedded oscillator circuit 526 and load modulator circuit 532 on the implant 500 can be pulsed in preference to being driven continuously. This option would (a) reduce the power requirement of the reader circuit, (b) reduce the likelihood of the reader coils overheating and shorting, and (c) increase the read range.

Further, increasing the effective read range of the system also can be achieved by driving and reading the embedded circuit independently. Increasing or adding capacitance in the strain gauge circuitry may permit enough energy storage to get sufficient operation to read the signal. If the circuit is energized sufficiently to provide a signal for sufficient time to be read at least one time by the reader then the reader drive can be pulsed in preference to being driven continuously. This option would (a) reduce the power requirement of the reader circuit, (b) reduce the likelihood of the reader coils overheating and shorting, (c) permit immediate isolation of the read signal from the reader signal to eliminate some of the filtering network in the reader, (d) permit the use of different coils for transmitting and receiving offering better tuning of the coils to read the particular transmitted frequencies, and (e) eliminate the issue of the reader signal affecting the embedded circuitry.

The invention further includes a method of health monitoring in a patient using electromagnetic telecommunication and/or wireless powering of a medical device generated from an external flexible dual coil reader device. The unique design of the reader system improves the receiving properties of telemetry coil arrangements for the reception of data signals in particular in orthopaedic implants. The method can be used to perform effective monitoring, management and tailoring of treatments for patients through interpreting the telemetric data received from a telemetric implant. The flexible dual coil reader head generates a magnetic field which has the ability to power a telemetric implant that is in an oblique position, i.e. ranging from a parallel to an orthogonal position. The ability to focus the electromagnetic field by altering the angle between the pair of coils is beneficial in situations where the implant is orientated such that it is difficult to power with conventional reader systems.

In order to conserve power, the RF telemetry system is only activated periodically when the reader is brought in close proximity of the implant; with the period of activation being sufficiently short so as to allow a reasonably prompt response of the implant to a request for a communication session by the external device. The addition of both on-board audible and visual signal "OK" light emitting diode (LED) indicators on the reader and/or the transmitter coils simplifies the process of locating and powering the internal telemetric implant, indicating the strength of the coupling between the receiver and transmitter coils, and informing the user of acquiring a reliable measurement related to the sensor when the implant is engaged.

The hand-held flexible dual coil reader system described herein is equipped with a signal "OK" LED feedback system for optimizing its position relative to the telemetric implant. The reader is also capable of simultaneously powering and reading an implantable telemetric implant in a wireless manner by inductively coupling energy from an external pair of reader (transmitter) coils to an internal power receiver coil housed on the implant. An inductive power supply is advantageous for instrumented implants because the measuring time is not limited and highly toxic materials, used in batteries, are avoided. Magnetic near field coupling can be utilized to transfer power to the internal receiver coil. The external transmitter coil is driven with an AC current between 119 and 135 kHz generating an AC magnetic field. When the receiver coil is placed in this field an AC voltage is generated on it. The telemetric implant is only activated when it is within the interrogation zone of the reader. When the implant is not being read, it is in "sleep" mode.

The reader described herein is capable of powering and reading a telemetric implant either independently or simultaneously. If the implant receiver coils are powered independently, the charge built up can be stored in a capacitor located on the telemetric implant. In this situation, the implant operates like a "flashgun" telemetering data to the user.

The telemetric implant may use analog or digital technology for measurement of physical characteristics of an implant, such as a load on an intramedullary nail or a bone plate. Additionally, the particular construction of the telemetric system is applicable to measurement of variables other than implant load. As examples, the devices described herein may be well suited for the measurement of implant micromotion, alkalinity, temperature, pressure, etc.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A telemetric system comprising:
a. a telemetric implant;
b. a reader unit adapted to read signals from the telemetric implant;
c. an antenna adapted for connection to the reader unit and to receive signals from the telemetric implant, the antenna having a first coil, a second coil, and a connector, the first coil being electrically connected to the second coil, and the connector allowing for movement of the first and second coils relative to each other; and
d. a mounting assembly having a first portion and a second portion, the first coil mounted to the first portion and the second coil mounted to the second portion, the connector allowing movement of the first portion relative to the second portion.

2. The telemetric system of claim 1, wherein the antenna is configured such that movement of the first coil or the second coil changes a shape of a magnetic field produced by said coils.

3. The telemetric system of claim 1, wherein the antenna is configured such that movement of the first coil or the second coil causes the antenna to conform to a mammalian tissue surface.

4. The telemetric system of claim 1, wherein the antenna is configured to power and read data from the telemetric implant from an oblique angle with respect to the telemetric implant.

5. The telemetric system of claim 1, wherein the first coil and the second coil are housed in a flexible polymer.

6. The telemetric system of claim 1, wherein the first coil and the second coil are housed in a pouch.

7. The telemetric system of claim 1, further comprising a component selected from the group consisting of a computing device, a signal generator, a power supply, an audible feedback system, and a visual indicator.

8. The telemetric system of claim 1, further comprising at least one additional antenna coil.

9. The telemetric system of claim 1, wherein the antenna further comprises at least one ferrite component.

10. The telemetric system of claim 1, wherein the reader unit comprises a microcontroller, a coil driver and reader, a frequency counter, and an amplifier, and wherein the telemetric implant comprises a power supply circuit, an oscillator circuit, and a load modulator circuit.

11. The telemetric system of claim 1, wherein the antenna is configured to send radio-frequency power to the telemetric implant and to receive data from the telemetric implant.

12. The telemetric system of claim 1, wherein the connector comprises a hinge.

13. The telemetric system of claim 9, wherein the at least one ferrite component is located between the first coil and the second coil.

14. The telemetric system of claim 1, wherein the connector is configured to orient the first coil relative to the second coil such that the antenna conforms to a tissue surface covering the telemetric implant.

15. The telemetric system of claim 1, wherein the first coil and the second coil are movable to communicate with the telemetric implant from either (i) a parallel orientation with respect to the telemetric implant or (ii) an orthogonal orientation with respect to the telemetric implant.

16. A telemetric system comprising:
   a telemetric implant comprising a power supply circuit, an oscillator circuit, and a load modulator circuit;
   a reader unit adapted to read signals from the telemetric implant, the reader unit comprising a microcontroller, a coil driver and reader, a frequency counter, and an amplifier; and
   an antenna adapted for connection to the reader unit and to receive signals from the telemetric implant, the antenna having a first coil, a second coil, and a connector, the first coil being electrically connected to the second coil, and the connector allowing for movement of the first and second coils relative to each other.

17. A telemetric system comprising:
   a telemetric implant;
   a reader unit adapted to read signals from the telemetric implant; and
   an antenna adapted for connection to the reader unit and to receive signals from the telemetric implant, the antenna having a first coil, a second coil, and a connector, the first coil being electrically connected to the second coil, and the connector allowing for movement of the first and second coils relative to each other,
   wherein the antenna is configured to send radio-frequency power to the telemetric implant and to receive data from the telemetric implant.

* * * * *